US007049094B2

(12) United States Patent
Young et al.

(10) Patent No.: US 7,049,094 B2
(45) Date of Patent: May 23, 2006

(54) METHODS FOR IDENTIFYING MODULATORS OF N-TYPE ION CHANNEL INACTIVATION

(75) Inventors: Kathleen H. Young, Newtown, PA (US); Kenneth J. Rhodes, Neshanic Station, NJ (US)

(73) Assignee: Wyeth, Madison, NJ (US)

( * ) Notice: Subject to any disclaimer, the term of this patent is extended or adjusted under 35 U.S.C. 154(b) by 491 days.

(21) Appl. No.: 10/051,841

(22) Filed: Jan. 17, 2002

(65) Prior Publication Data
US 2003/0077671 A1 Apr. 24, 2003

Related U.S. Application Data

(63) Continuation of application No. 09/295,999, filed on Apr. 21, 1999, now abandoned.

(51) Int. Cl.
*C12N 15/00* (2006.01)
*C12N 15/12* (2006.01)
*C12N 15/63* (2006.01)
*C07K 14/00* (2006.01)
*C07H 21/04* (2006.01)

(52) U.S. Cl. .................. 435/69.1; 435/320.1; 435/325; 424/192.1; 424/185.1; 536/23.5; 530/350

(58) Field of Classification Search ............... 536/23.5; 435/69.1, 320.1, 325; 530/350; 424/192.1, 424/185.1
See application file for complete search history.

(56) References Cited

U.S. PATENT DOCUMENTS

| 5,776,689 A | 7/1998 | Karin et al. |
|---|---|---|
| 5,856,155 A * | 1/1999 | Li ............................... 435/455 |
| 6,080,557 A | 6/2000 | Sims et al. |

FOREIGN PATENT DOCUMENTS

| WO | WO 95/34646 | 12/1995 |
| WO | WO 97/31112 | 8/1997 |

OTHER PUBLICATIONS

Mickle JE et al. Genotype-phenotype relationships in cystic fibrosis. Med Clin North Am. May 2000;84(3):597-607.*
Voet et al. Biochemistry. 1990. John Wiley & Sons, Inc. pp. 126-128 and 228-234.*
Yan et al., Two-amino acid molecular switch in an epithelial morphogen that regulates binding to two distinct receptors. Science 290: 523-527, 2000.*
Tamkun,M.M., Knoth,K.M., Walbridge,J.A., Kroemer,H., Roden,D.M. and Glover,D.M. Molecular cloning and characterization of two voltage-gated K+ channel cDNAs from human ventricle. FASEB J. 5 (3), 331-337 (1991).*
Leicher,T., Roeper,J., Weber,K., Wang,X. and Pongs,O. Structural and functional characterization of human potassium channel subunit beta 1 (KCNA1B). Neuropharmacology 35 (7), 787-795 (1996).*
Christie,M.J., Adelman,J.P., Douglass,J. and North,R.A. Expression of a cloned rat brain potassium channel in Xenopus oocytes. Science 244 (4901), 221-224 (1989).*
K. Young et al., "Identification of a Calcium Channel Modulator Using a High Throughput Yeast Two-Hybrid Screen," *Nature Biotechnology*, 16: 946-950 (1998).
B. Ozenberger, et al., "Functional Interaction of Ligands and Receptors of the Hematopoietic Superfamily in Yeast," *Molecular Endocrinology*, 9(10): 1321-1329 (1995).
R. Scannevin, et al., "Cytoplasmic Domains of Voltage-Sensitive K+ Channels Involved in Mediating Protein-Protein Interactions," *Biochemical and Biophysical Research Communication*, 232(RC976333): 585-589 (1997).
J. Xu, et al., "Auxiliary Subunits of Shaker-Type Potassium Channels," *TCM*, 8(5): 229-234 (1998).
S. Heineman, et al., "The Inactivation Behavior of Voltage-Gated K-Channels may be Determined by Association of α- and β-subunits," *J. Physiology*, 88: 173-180 (1994).
E. Isacoff, et al., "Putative Receptor for the Cytoplasmic Inactivation Gate in the Shaker K+ Channel," *Nature*, 353(5): 86-90 (1991).
R. MacKinnon, et al., "Functional Stoichiometry of Shaker Potassium Channel Inactivation," *Science*, 262(29): 757-759 (1993).
W. Zagotta, et al., "Restoration of Inactivation in Mutants of Shaker Potassium Channels by a Peptide Derived from ShB," *Science*, 250: 568-571 (1990).
T. Hoshi, et al., "Biophysical and Molecular Mechanisms of Shaker Potassium Channel Inactivation," *Science*, 250: 533-538 (1990).
Angelides, K.J. and T.J. Nutter, *J. Biol. Chem.*, 258:11958-11967 (1983).
Butterworth, J.F. and G.R. Strichartz, *Anesthesiology* ,72:711-734, (1980).

(Continued)

Primary Examiner—Joseph Murphy
(74) Attorney, Agent, or Firm—Nixon Peabody LLP; Raymond Van Dyke

(57) ABSTRACT

Methods and compositions for identifying compounds which disrupt the functional interaction of an intracellular receptor region of an α-subunit of a voltage-gated ion channel and an amino-terminal inactivation region of an ion channel protein are disclosed. Compounds that disrupt the functional or binding interaction of these two regions have significant modulatory effects on ion channel activity, and thus are likely to be useful for treating and/or preventing a wide variety of diseases and pathological conditions associated with ion channel dysfunction. Such conditions include, for example, neurological disorders, cardiac diseases, metabolic diseases, tumor-driven diseases, and autoimmune diseases.

4 Claims, 11 Drawing Sheets

OTHER PUBLICATIONS

Figure 3A:
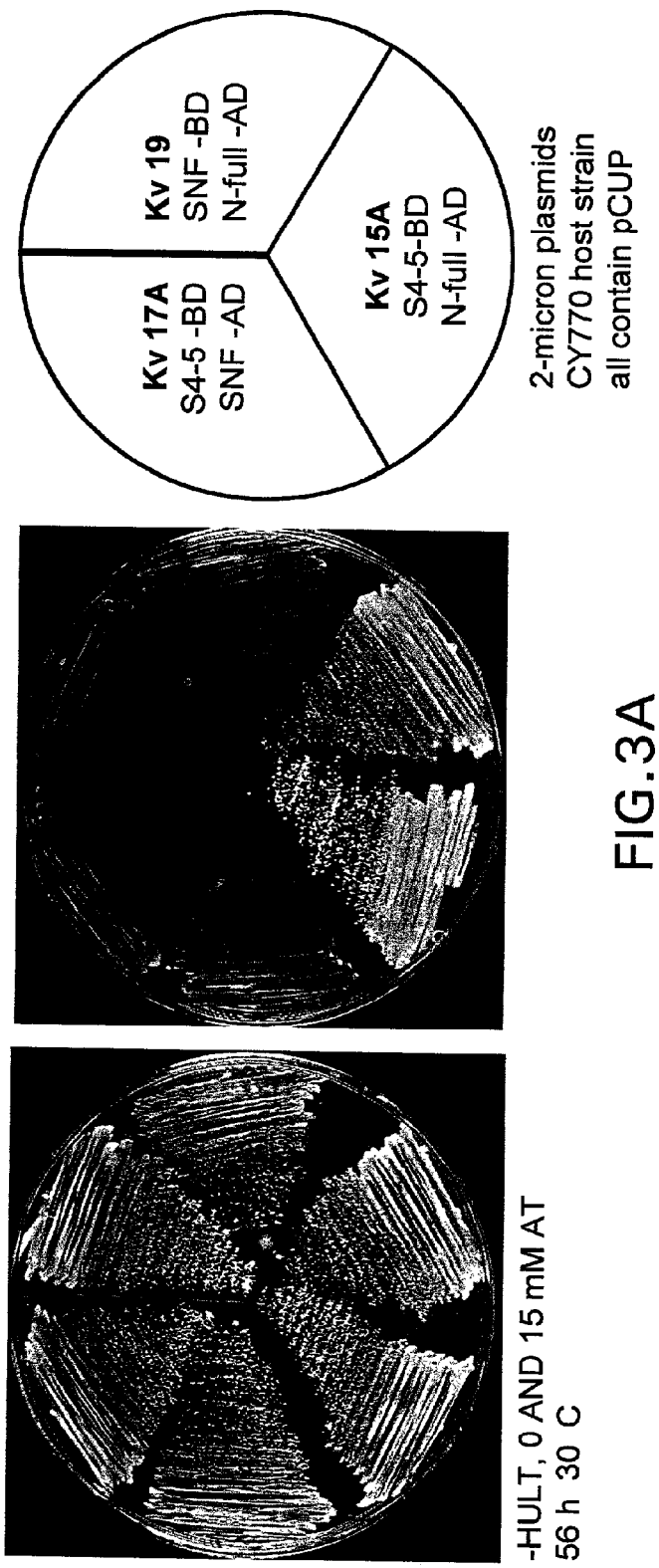

Crow, T., *Trends Neurosci.* 11:136-142 (1988).
Heginbotham, L. et al., *Science*, 258:1152-1155 (1992).
Hille, B., *Ionic Channels of Excitable Membranes*, (Sinauer Press, Sunderland, MA) 1992.
Hodgkin, A.L. and Huxley, A.F., *J. Physiol.*, 117:500-544 (1952).
Jessell, T.M. and Kandel, E.R., *Cell*, 72(Suppl.):1-30 (1993).
Miller, C., *Science*, 252:1092-1096 (1991).
Muniz, Z.M. et al., *Biochemistry*, 31:12297-12303 (1992).
Aronheim, A. et al., *Cell*, 78:949-961 (1994).
Aronheim, A. et al., *Mol. Cell. Biol.*, 17(6):3094-3102 (1997).
Avruch, J., *Mol. Cell. Biochem.*, 182(1-2):31-48 (1998).
Boguski, M.S. and McCormick, F.*Nature*, 366:643-654 (1993).
Broder, Y.C. et al., *Curr. Biol.*, 8(20):1121-1124 (1998).
Buss, J.E. et al., *Mol. Cell. Biol.*, 8:3960-3963 (1988).
Carter-Su, C. and Smit, L.S., *Hormone Res.*, 53:61-83 (1998).
Durrell, S.R. and Guy, H.R., *Biophys. J.*, 62:238-250 (1992).
Fields, S. and Song, O.-K., *Nature*, 340:245-246 (1989).
Li, M. et al., *Science*, 257:1225-1230 (1992).
Miller et al., *Genetic Engineering*, Principles and Methods, 8:277-298, Setlow, J.K. and Hollaender, A. (eds), Plenum Press, NY (1986).
Parcei, D. N., and Dolly, J.O., *Biochem. J.*, 257:899-903 (1989).
Picard, D. et al., *Gene*, 86:257-261 (1990).
Ruppersberg, J.P. et al., *Nature*, 353:657-660 (1991).
Shi, G. et al., *Neuron*, 16:843-852 (1996).
Strichartz, G. et al., *Ann. Rev. Neurosci.*, 10:239-267 (1987).
Wilson, T.E. et al., *Science*, 252:1296-1300 (1990).
Albus, H. and Williamson, R., *Epilepsia*, 39(2):124-139 (1998).
Altschul, S.F. and Gish, W., *Local alignment statistics*, Doolittle (ed.), *Methods in Enzymology* 266:460-480 (1996).
Altschul, S.F., *J. Mol. Biol.*, 215:403-410 (1990).
Ausubel, F.M. et al. (eds), "Current Protocols in Molecular Biology," *John Wiley & Sons, Inc.* Sections 2.10 and 6.3-6.4 (1995).
Chardin, P. et al., *Science*, 260:1338-1343 (1998).
Durfee, T., et al., *Gene Devel.*, 7:555-569 (1993).
Finney, M., *Current Protocols in Molecular Biology*, Wiley & Sons, NY, 1993.
Force, T. and Bonventre, J.V., *Hypertension* 31(Part 2):152-161 (1998).
Gish, W. and States, D.J., *Nature Genetics*, 3:266-272 (1993).
Gustin, M.C., et al., *Microbiol. Mol. Biol. Rev.*, 62(4):1264-1300 (1998).
Hancock, J.F. et al., *EMBO J.*, 10(13):4033-4039 (1991).
Karlin, S. and Altschul, S.F., *Proc. Natl. Acad. Sci. USA*, 90:5873-5877 (1993).
Lai, C.-C. et al., *Mol. Cell. Biol.*, 13(3):1345-1352 (1993).
Quilliam, L.A. et al., *Proc. Natl. Acad. Sci. USA*, 91:8512-8516 (1994).
Sambrook, J., Fritsch, E.F., and Maniatis, T. (eds), "Molecular Cloning: A Laboratory Manual," *Cold Spring Harbor Laboratory Press, Cold Spring Harbor, NY, Chapters 9 and 11* (1989).
Shaw, G., *BioEssays*, 18:35-46 (1996).
Whitmarsh, A.J. and Davis, R.J., *J. Mol. Med.*, 74(10):589-607 (1996).
Frey, H.-H. and Bartels, I., *Epilepsy Res.*, 27:151-164 (1997).
Isacoff, E.Y., et al., *Nature*, 353:86-90 (1991).
Rose, M.D., et al., *Methods in Yeast Genetics, Cold Spring Harbor Laboratory Press, Cold Spring Harbor, NY*, 1990.
Walsh, J., *Proceeding: Intl. Symp. Lab. Auto. Robotics*, Boston, MA, Oct. 19-22, 1997.
Stephens, G.J. et al., *FEBS Letters*, 378:250-252 (1996).
Wang, Z. et al., *J. Biol. Chem.*, 271(45)28311-28317 (1996).
Yan, M. et al., *Science*, 290:523-527 (2000).
Choi, K.L. et al., *Proc. Natl. Acad. Sci. USA*, 88:5092-5095 (1991).

\* cited by examiner

```
hKv1.1LOOP    QILGQTLKASMRELGL
hKv1.2LOOP    QILGQTLKASMRELGL
hKv1.3LOOP    QILGQTLKASMRELGL
hKv1.5LOOP    QILGKTLQASMRELGL
hKv1.6LOOP    QILGKTLQASMRELGL
hKv1.4LOOP    QILGHTLRASMRELGL
hKv3.4LOOP    RVLGHTLRASTNEFLL
```

FIG. 1

```
hKvβ1N     -MQVSIACTEHNLKSRNGEDRLLSKQSSTAP-
hKvβ1bN    MHLYKPACADIP-SPKLGLPKSSESALKCRW-
hKvβ3N     MHLYKPACADIP-SPKLGLPKSSESALKCRW-
hKv3.4N    --MISSVCVSSYRGRKSGNKPPSKTCLKEEMA
hKvβ1CN    -MLAARTGAAGSQISEENTKLRRQSGFSVAG-
hKv1.4N    -MEMAMVSAESS-GCNSHMPYGYAAQARARER
```

FIG. 2

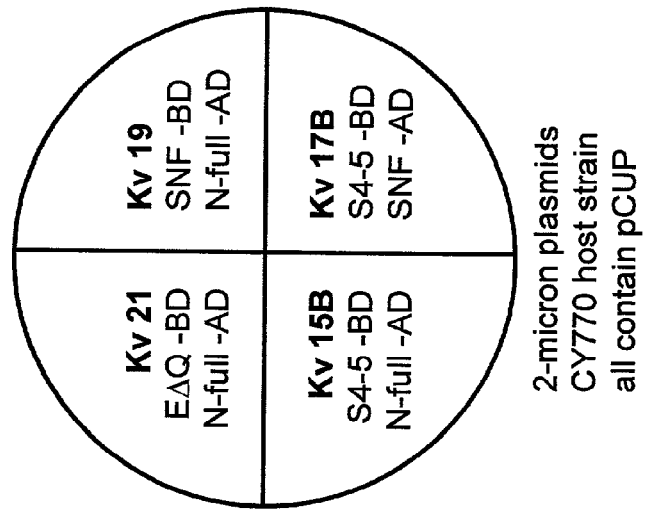
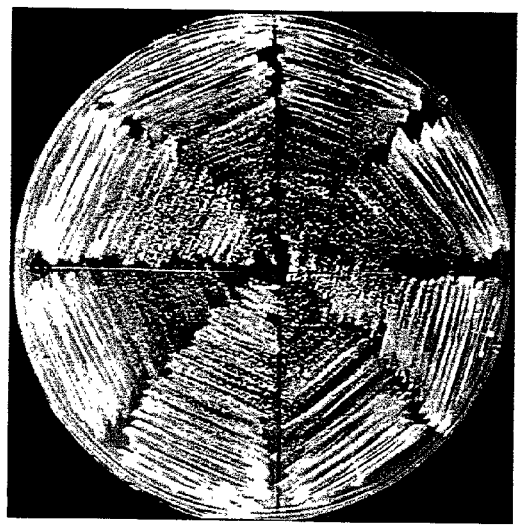
FIG. 3B

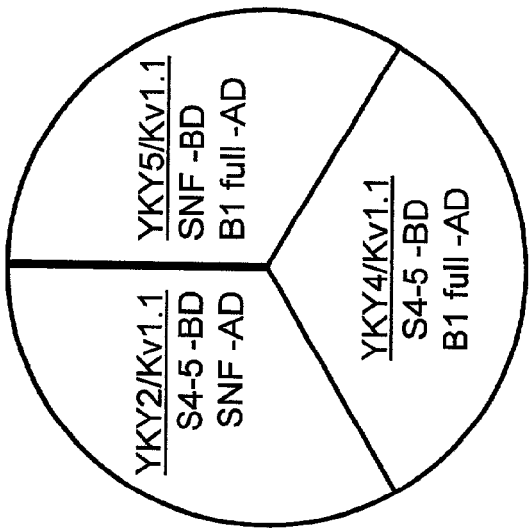
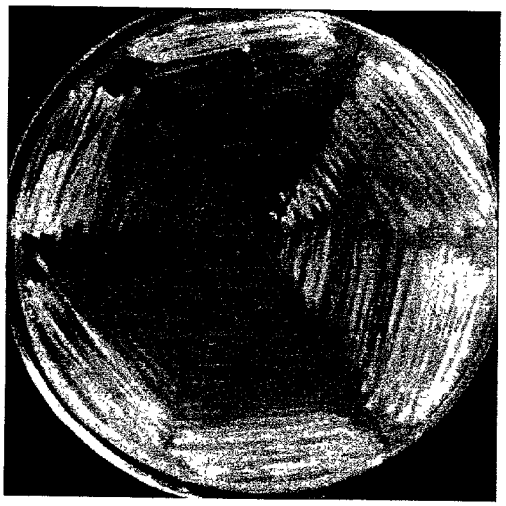
Potassium Channel (Kv 1.1/B1)
[S4-5 loop / B1 full length interaction]
Histidine Prototrophy
-HULT, 0 or 20 mM AT

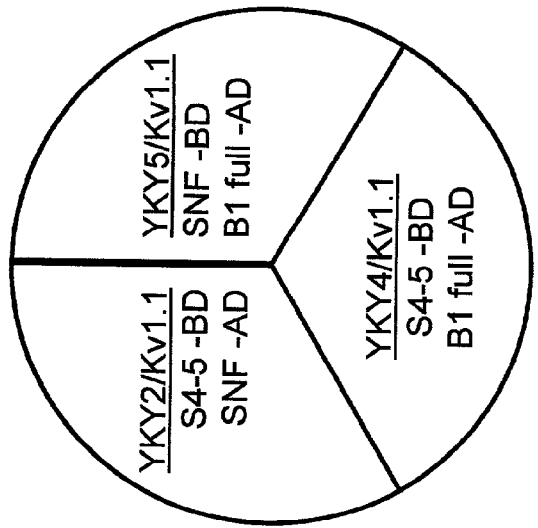
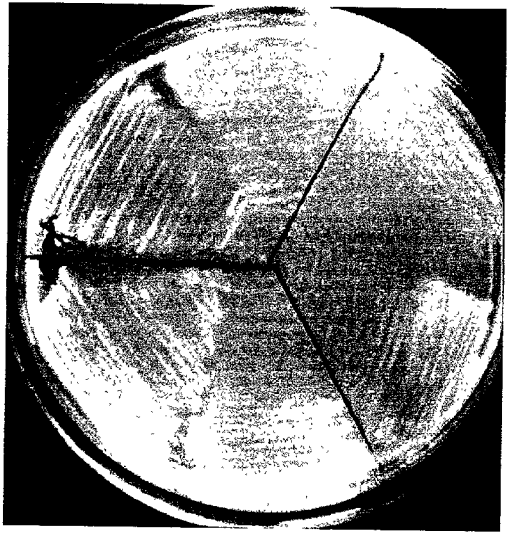
FIG. 4B

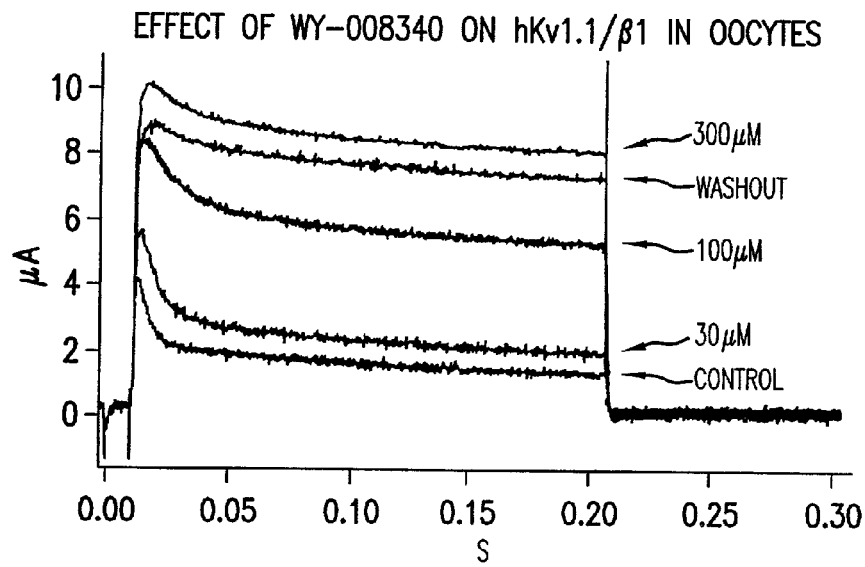
FIG. 7A
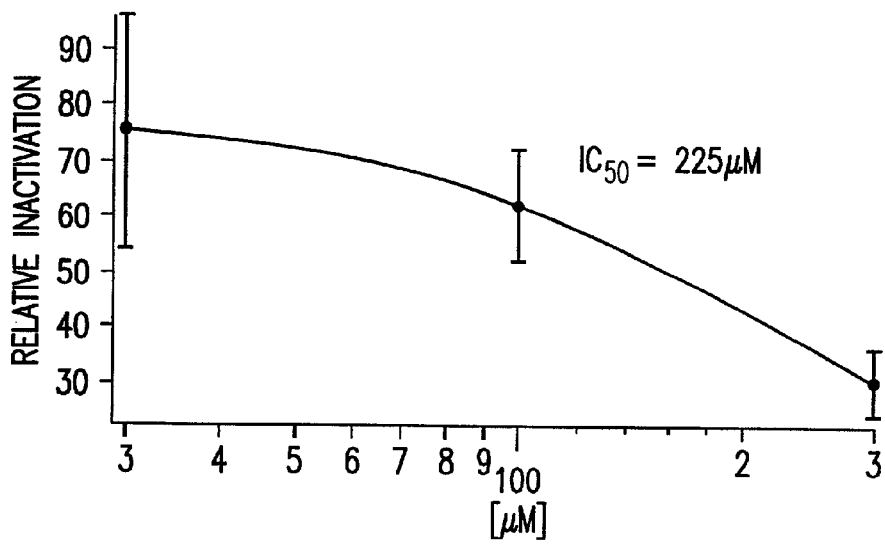
FIG. 7B
|  | REL. INACTIVATION | | CURRENT AMPLITUDE | |
|---|---|---|---|---|
|  | MEAN | SEM | MEAN | SEM |
| CONTROL | 100.00 | 0.00 | 100.00 | 0.00 |
| 30μM | 75.23 | 20.86 | 118.40 | 16.30 |
| 100μM | 61.99 | 9.67 | 174.64 | 16.58 |
| 300μM | 29.59 | 5.48 | 205.53 | 34.03 |
| WASHOUT | 24.90 | 6.73 | 188.27 | 31.18 |
n = 3,4
FIG. 7C

METHODS FOR IDENTIFYING MODULATORS OF N-TYPE ION CHANNEL INACTIVATION

This application is a Continuation of U.S. application Ser. No. 09/295,299 filed Apr. 21, 1999, now abandoned.

The present invention relates to methods and compositions for identifying compounds which modulate N-type inactivation of voltage-gated ion channels.

BACKGROUND OF THE INVENTION

Ion channels are transmembrane proteins that regulate entry of various ions into cells from the extracellular matrix. Ion channels are physiologically important, playing essential roles in regulating intracellular levels of various ions and in generating action potentials in nerve and muscle cells. Hille, B., *Ionic Channels of Excitable Membranes* (Sinauer, Sunderland, Mass., 1992). Passage of ions through ion channels is characterized by selective filtering and by a gating-type mechanism which produces a rapid increase in permeability. Angelides, K. J. and T. J. Nuttov, *J. Biol. Chem.* 258: 11858–11867 (1981). Ion channels may be either voltage-gated, implying that current is gated (or regulated) by membrane potential (voltage), or chemically-gated (e.g., acetylcholine receptors and γ-aminobutyric acid receptors), implying that current is gated primarily by binding of a chemical rather than by the membrane potential. Butterworth, J. F. and G. R. Strichartz, *Anesthesiology* 72:711–734 (1980). An important characteristic of certain voltage-gated channels is inactivation: soon after opening they close spontaneously, forming an inactive channel that will not reopen until the membrane is repolarized. Miller, C., *Science* 252:1092–1096 (1991). Rapidly inactivating ("A-type") voltage-gated ion channels control the rate at which excitable cells reach the threshold for firing action potentials and thus are key regulators of neuronal excitability. B. Hille, supra.

Many voltage-gated ion channels that generate action potentials have been cloned and sequenced, and all have a remarkably similar structure. A typical potassium channel contains four copies of an approximately 600-amino-acid polypeptide, each of which has six membrane-spanning α-helices. Heginbotham, L., et al., *Science* 258:1152 (1992). Sodium and calcium channels are single polypeptides of about 2000 amino acids that contain four homologous domains, each comprised of six transmembrane domains which are similar in sequence and structure to a potassium channel protein. These domains are connected and flanked by shorter stretches of nonhomologous residues. Jessell, T. M. and E. R. Kandel, *Neuron* 10(Supp):1–3 (1993). It is believed that the α-helical structures provide conformational flexibility for the ion channel which is functionally responsible for the channel's gating mechanism. See Heinemann, S., et at., *J. Physiol.* 88:173–180 (1994).

In addition to affecting action potentials, ion channels facilitate other important physiological functions such as cardiac pacemaking, neuron bursting, and possibly learning and memory. Crow, T., *Trends Neurosci.* 11:136–142 (1988); Hodgkin, A. L. and Huxley, A. F., *J. Physiol.* 117:500–544 (1952). In addition to their involvement in normal cellular homeostasis, ion channels are associated with a variety of disease states and immune responses. Diseases believed to be associated with dysfunction of ion channels include neurological disorders, metabolic diseases, cardiac diseases, tumor-driven diseases, and autoimmune diseases.

Due to the importance of ion channels in both normal cellular homeostasis and disease, considerable research effort has focused on ion channels, and particularly on identifying compounds which affect their function. Thus, several techniques have been developed to evaluate the gating mechanism of ion channels and the mode of action of channel-drug interaction. Electrophysiological recording has been used to define the roles of ion currents, and especially potassium and sodium currents, in generating action potentials in excised nerves. Hodgkin, A. L. and A. F. Huxley, supra. This technique, however, is not suitable for mass screening of compounds due to its technical complexity and the requirement of a high degree of sophistication to generate reproducible results. Radioligand binding assays have been used to characterize the site of action of various classes of ion channel blockers. However, the availability of radiolabelled ligands, the level of nonspecific binding, and the physico-chemical property of the molecules have limited the application of this technique. Strichartz, et al., *Ann. Rev. Neurosci.* 10:239–67 (1987). Fluorescent-labelled neurotoxin probes have also been used to map the molecular structure of the functional site of the channel, but have not gained general popularity for broader use. Angelides, K. A. and T. J. Nuttov, *J. Biol. Chem.* 256:11958–11967 (1983).

Recently, a modified yeast "two-hybrid" system has been developed to identify compounds that bind to either the $NH_2$-terminal multimerization domain (commonly referred to as the "NAB" or "T1" domain) on the α-subunit of a Shaker-like potassium channel or to the "core" domain of the β-subunit of the potassium channel, thereby preventing the α/β subunit interaction. See U.S. Pat. No. 5,856,155 (M. Li), issued Jan. 5, 1999; and PCT App. No. PCT/US97/02292, published Aug. 28, 1997 (WO 97/31112). Unfortunately, significant inherent limitations in this system may prevent or limit its practical application. Such limitations include, for example, the extraordinarily tight nature of the α-NAB/β-core interaction (which survives such harsh treatments as detergent extraction and affinity chromatography), the limited applicability to potassium channels whose activity requires interaction between the NAB domain of the α-subunit and the core domain of the β-subunit, and, most importantly, the potentially significant inhibitory effect such compounds would have on potassium channel surface expression. [Regarding the tight association of α-and β-subunits, see Parcej, D. N., and J. O. Dolly, *Biochem. J.* 257:899–903 (1989) and Muniz, Z. M., et al., *Biochemistry* 31:12297–12303 (1992).] With respect to the latter limitation, β-subunits have been shown to promote N-linked glycosylation and surface expression of α-subunits. Shi, G., et al. *Neuron* 16:843–852 (1996). Thus, one would expect compounds that bind to the core domain of the β-subunit to block these chaperone-like effects, thereby reducing, if not preventing, the biosynthesis of functional potassium channels. By affecting the abundance or distribution of potassium channels in excitable membranes, such compounds would essentially act as ion channel blockers, and thus would likely have adverse neurophysiological effects. Finally, any compound that can effectively block the strong α-NAB/β-core binding interaction (i.e., compounds identified using this modified yeast two-hybrid system) must themselves have extremely high binding affinity for potassium channel subunits, and thus would likely be toxic to a mammalian host.

In view of the complexity of ion channel pharmacology and its attractiveness as a target site for the discovery of novel therapeutic compounds, there exists a need for an alternative technique which will enable the large-scale screening of compounds for ion channel modulatory activity in a simple and reliable manner. The present invention fulfills these and other needs.

SUMMARY OF THE INVENTION

The present invention provides several novel methods and compositions for identifying compounds which affect binding between two key regulatory regions of voltage-gated ion channels. More specifically, the invention relates to methods and compositions for identifying compounds which affect the binding of an intracellular receptor region of an α-subunit of a voltage-gated ion channel and an amino-terminal inactivation region of an ion channel protein. Compounds that disrupt or facilitate the functional or binding interaction of these two key regulatory regions have significant modulatory effects on ion channel activity, and thus are likely to be useful for treating and/or preventing a wide variety of diseases and pathological conditions associated with ion channel dysfunction. Such conditions include, for example, neurological disorders, cardiac diseases, metabolic diseases, tumor-driven diseases, and autoimmune diseases. Many of these compounds are expected to have potent anticonvulsant and neuroprotective properties which will prove especially useful for the prevention and/or treatment of neurodegenerative disorders such as epilepsy, stroke, cerebral ischemia, cerebral palsy, hypoglycemia, Alzheimer's disease, Huntington's disease, asphyxia and anoxia, as well as for the treatment of neuropathic pain, spinal cord trauma, and traumatic brain injury.

In one aspect, the invention provides methods of evaluating and screening candidate compounds for the ability to affect binding of an intracellular receptor region of an α-subunit and an amino-terminal inactivation region of an ion channel protein. The methods comprise contacting the compound with the intracellular receptor region and the amino-terminal inactivation region, and determining the ability of the compound to interfere with or facilitate the functional interaction or binding of these two regions. A decrease in binding in the presence of the compound compared to the binding in the absence of the compound indicates that the compound inhibits functional interaction or direct binding between these two regulatory regions. Similarly, an increase in binding in the presence of the compound compared to the binding in the absence of the compound indicates that the compound facilitates functional interaction between these two regulatory regions.

In another aspect, the invention provides methods for evaluating or screening candidate compounds comprising adding a candidate compound to a modified host cell and comparing the expression of a reporter gene in the presence and absence of the compound. A decrease (or increase) in expression of the reporter gene is an indication that the compound inhibits (or promotes) functional or binding interaction between the intracellular receptor region and the amino-terminal inactivation region.

In yet another aspect, the invention provides modified host cells and methods for evaluating or screening candidate compounds for ion channel modulatory activity. The modified host cells contain a first hybrid protein comprising a DNA-binding domain of a transcriptional activator in polypeptide linkage to either (i) an intracellular receptor region of an α-subunit of a voltage-gated ion channel or (ii) an amino-terminal inactivation region of an ion channel protein, and a second hybrid protein comprising an activation domain of a transcriptional activator in polypeptide linkage to the intracellular receptor region if the DNA-binding domain is in polypeptide linkage to the amino-terminal inactivation region or to the amino-terminal inactivation region if the DNA-binding domain is in polypeptide linkage to the intracellular receptor region. The modified host cell may optionally comprise a reporter gene whose expression is inhibited in the presence of an inhibitor of N-type inactivation.

In still another aspect, the modified host cell contains a first hybrid protein comprising an intracellular receptor region of an α-subunit of a voltage-gated ion channel in polypeptide linkage to a first peptide of a peptide binding pair, and a second hybrid protein comprising an amino-terminal inactivation region of an ion channel protein in polypeptide linkage to a second peptide of the peptide binding pair, wherein binding interaction between the two peptides causes activation of a signal transduction pathway in the modified host cell. Activation of the signal transduction pathway does not occur in the presence of a molecule which inhibits binding of the intracellular receptor region and the amino-terminal inactivation region of an ion channel protein.

In other aspects, the invention provides polynucleotides, expression vectors, and host cells transfected or transformed with expression vectors containing nucleotide sequences which encode an intracellular receptor region of an α-subunit of a voltage-gated ion channel and an amino-terminal inactivation region of an ion channel protein, or biologically active fragments thereof.

BRIEF DESCRIPTION OF THE FIGURES

FIG. 1. Amino acid comparison of the intracellular receptor regions ("loops") of the human Kv1.2 ("hKv1.2"), human Kv1.3 ("hKv1.3"), human Kv1.4 ("hKv1.4"), human Kv1.5 ("hKv1.5"), human Kv1.6 ("hKv1.6") and human Kv3.4 ("hKv3.4") are shown in alignment with human Kv1.1 ("hKv1.1"). The black boxes indicate sequence identity; shaded boxes indicate conservative amino acid substitutions. The intracellular receptor regions of hKv1.1, hKv1.2, hKv1.3, hKv1.4, hKv1.5, hKv1.6, and hKv3.4 are designated as hKv1.1LOOP (SEQ ID NO:1), hKv1.2LOOP (SEQ ID NO:1), hKv1.3LOOP (SEQ ID NO:1), hKv1.4LOOP (SEQ ID NO:2), hKv1.5LOOP (SEQ ID NO:24), hKv1.6LOOP (SEQ ID NO:24), and hKv3.4LOOP (SEQ ID NO:25), respectively.

FIG. 2. Amino acid comparison of the amino-terminal inactivation regions ("N") of the human Kvβ1b ("hKvβ1b"; also known as "hKvβ1.2"), human Kvβ1c ("hKvβ1c"; also known as "hKvβ1.3"), human Kvβ3 ("hKvβ3"), human Kv1.4 ("hKv1.4"), and human Kv3.4 ("hKv3.4") are shown in alignment with human Kvβ1 ("hKvβ1"). The black boxes indicate sequence identity; shaded boxes indicate conservative amino acid substitutions. The amino-terminal inactivation regions of hKvβ1, hKvβ1b, hKvβ3, hKv3.4, hKvβ1c, and hKv1.4 are designated as hKvβ1N (SEQ ID NO:5), hKvβ1bN (SEQ ID NO:26), hKvβ3N (SEQ ID NO:26), hKv3.4N (SEQ ID NO:27), hKvβ1CN (SEQ ID NO:28), and hKv1.4N (SEQ ID NO:6), respectively.

FIG. 3. (a) Interaction of the amino terminal inactivation region and S4–S5 cytoplasmic receptor domain of Kv1.4: The placement of the Kv1.4 strain ("Kv15A") and two negative controls ("Kv17A" and "Kv19") are as depicted. BD and AD denote Gal4 DNA binding domain and activation domain fusion proteins, respectively. Two independent transformants for each strain are plated on plasmid retention media (left) and on positive selection media (histidine deficient medium +15 mM AT) (right). (b) Effect of EΔQ mutation in the Kv1.4 S4–S5 cytoplasmic receptor domain: The placement of the wild type Kv1.4 strain ("Kv 15a"), EΔQ strain ("Kv21"), and two negative control strains ("Kv19" and "Kv17B") are as depicted. BD and AD denote Gal4 DNA binding domain and activation domain fusion proteins, respectively. Two independent transformants for each strain are plated on plasmid retention media (left) and on positive selection media (histidine deficient medium +30 mM AT) (right).

FIG. 4 Interaction of Kv1.1β1/S4–S5 loop Kv1.1 interaction: The placement of the Kv1.1/β1 strain ("YKY4/Kv1.1") and two negative controls ("YKY2/Kv1.1" and "YKY5/Kv1.1") are as depicted. BD and AD denote Gal4 DNA binding domain and activation domain fusion proteins, respectively. (FIG. 4*a*) Two independent transformants for each strain are plated on (A) plasmid retention media (left), positive selection media (histidine deficient medium +20 mM AT); and plated on (FIG. 4*b*) plasmid retention media (left) and inverse-selection media containing 10 μg/ml cycloheximide (right).

FIG. 5. CYH2 Inverse selection rescue screen schematic: The Kv1.1 S4–S5 cytoplasmic receptor domain and Kvβ1 are expressed as fusion proteins to the DNA binding domain (BD) and the activation domain (AD), respectively, of the yeast Gal4 transcription activator protein. A negative control strain expressing unrelated but interacting yeast proteins ("SNF1" and "SNF4") in a similar manner. Functional interaction of the protein pair activates the downstream CYH2 counter-selection reporter gene, and confers cycloheximide sensitivity and attenuated cell growth. Disruption of the interaction (in the Kv1.1/β1 strain) by a small synthetic compound prevents the two-hybrid interaction, the CYH2 gene is not activated and cell growth is observed.

Figure 6A:
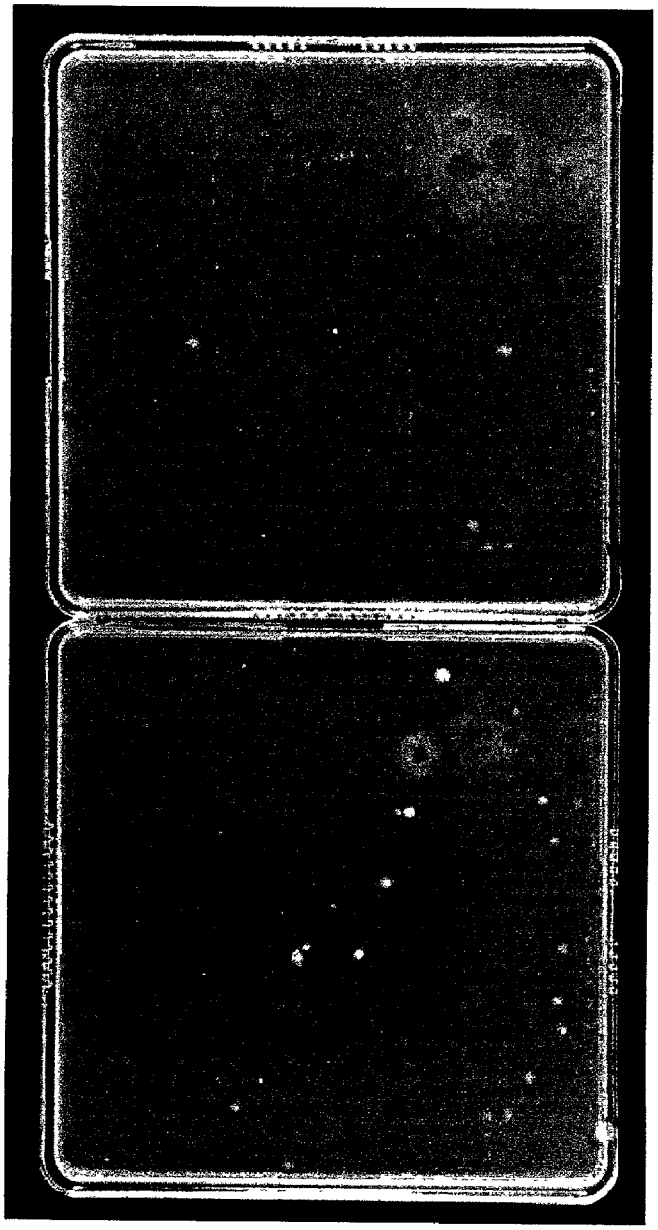
Figure 6B:
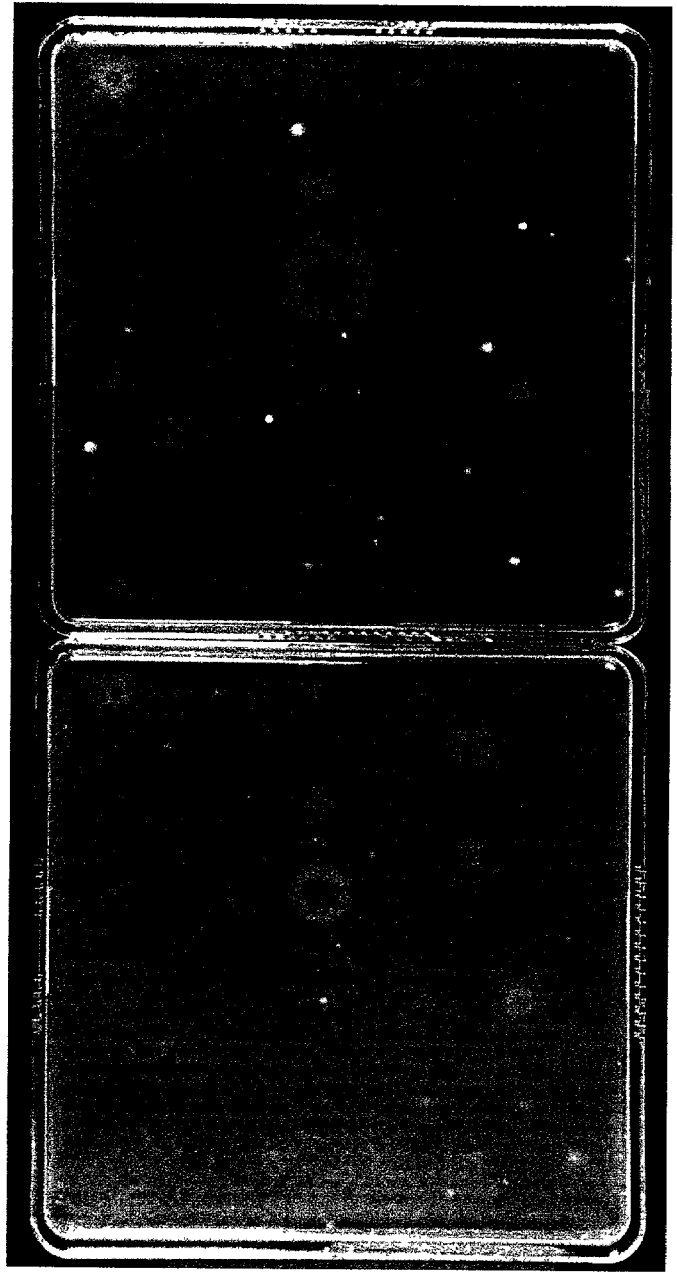
Figure 6C:
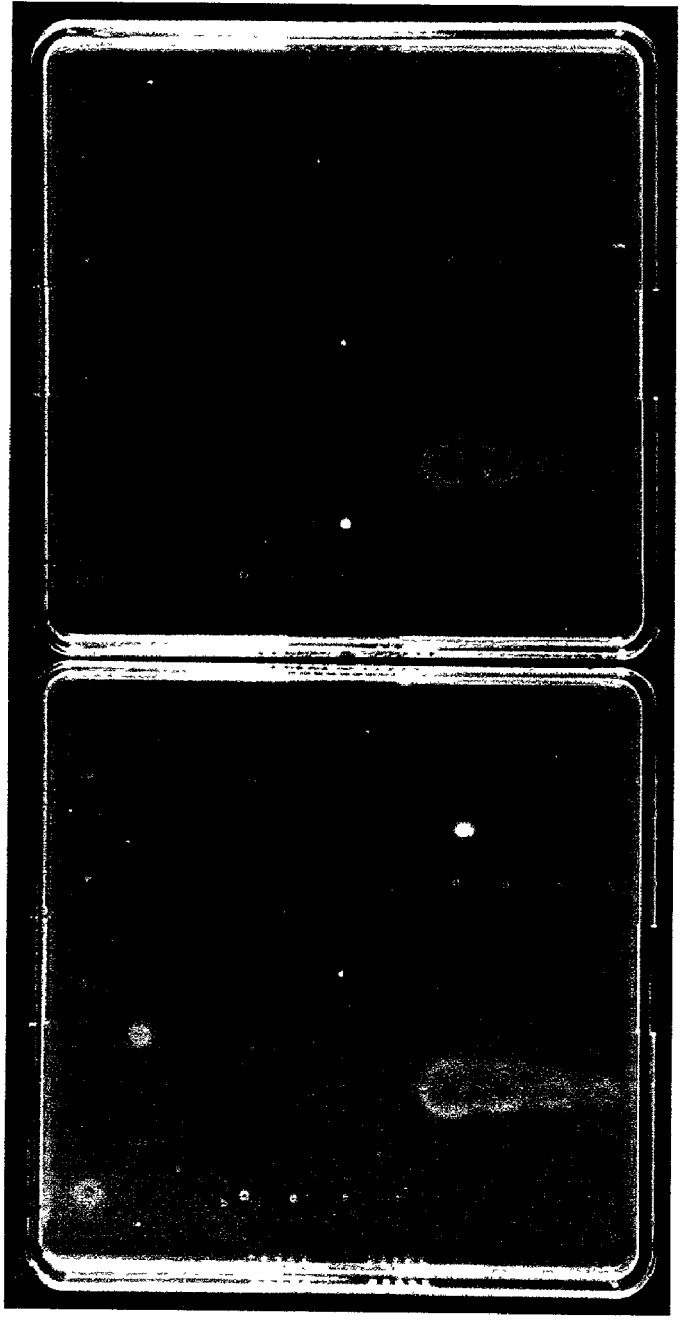

FIG. 6. Inverse-selection yeast two-hybrid based screen using a high throughput agar diffusion format: The Kv1.1/β1 yeast strain (TEST; strain YKY4/Kv1.1) was embedded in assay medium (SC-leu-trp-ura containing 11 _g/ml cycloheximide) at a density of $1 \times 10^5$ cells/ml. The negative control strain (CY856) was plated identically, but at $2 \times 10^4$ cells/ml. Approximately 2 _l of individual synthetic compound (9 mg/ml DMSO) is applied identically to the agar surface to the test and negative control plate in a 6×96 well array at a density of 572 compounds per plate (A), at a rate of approximately 15,000–30,000 compounds per day via a three day assay cycle. Assay plates were incubated at 30° C. for approximately 48 hours. Evidence of rescued yeast cell growth (halo effect) around the point of compound application was scored visually. Additionally, compounds that were obscured due to neighboring compound toxicity were individually retested. Compounds that demonstrated selective or differential rescue were scored as "positive." Compound induced growth was confirmed in an identical assay at a density of 55 compounds per plate (B), and using original compound stocks tested via titration using four concentrations (C). In all figures, the Kv1.1/β1 test strain (YKY4/Kv1.1) is shown on the left, and the negative control strain (CY856) is shown on the right.

FIG. 7. (FIG. 7a) Electrophysiological current recordings of inactivating channels expressed in *Xenopus* oocytes. *Xenopus* oocytes were injected with 0.5 ng of hKv1.1:10 ng of hKvβ1 mRNA transcribed in vitro using standard procedures (Sambrook et al, (1989) Molecular Cloning: A Laboratory Manual). Cells were challenged with families of voltage pulses of 200 ms duration ranging from −60 mV to 50 mV once every 2 min. Cells were exposed to each dose of "Wy-8340" ($C_{10}H_{15}NO$; 6-aminothymol or 4-amino-2-isopropyl-5-methylphenol) for 6 min and cumulative dose-response curves were performed. Relative inactivation was calculated by measuring the amplitude of the peak and steady-state currents, setting the inactivation (without compound) for each cell to 100% (i.e., maximum) and measuring the percent disinactivation with each dose of compound. (FIG. 7b) Concentration-response curves showing the effect of Wy-8340 on inactivation of hKv1.1 and hKvβ1 channels expressed in *Xenopus* Oocytes.

Figure 8C:
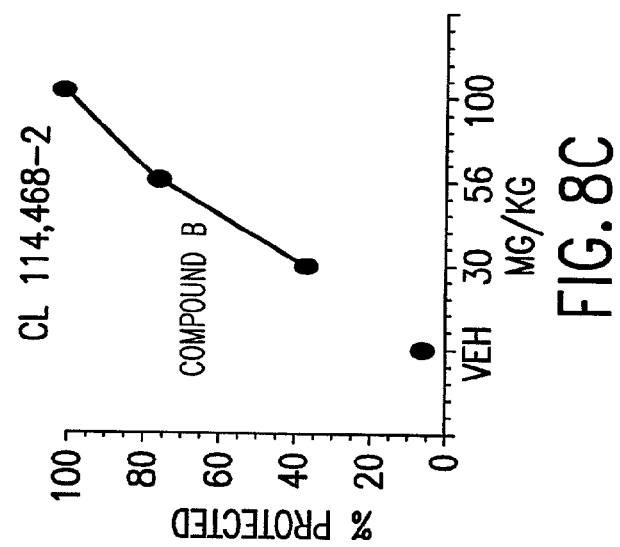
Figure 8B:
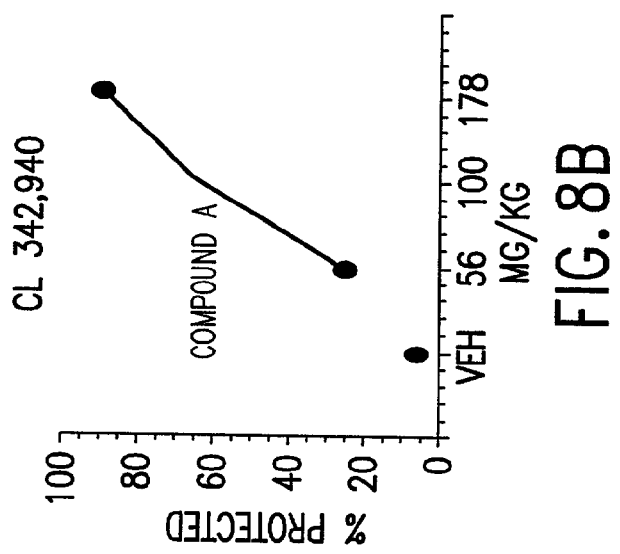
Figure 8A:
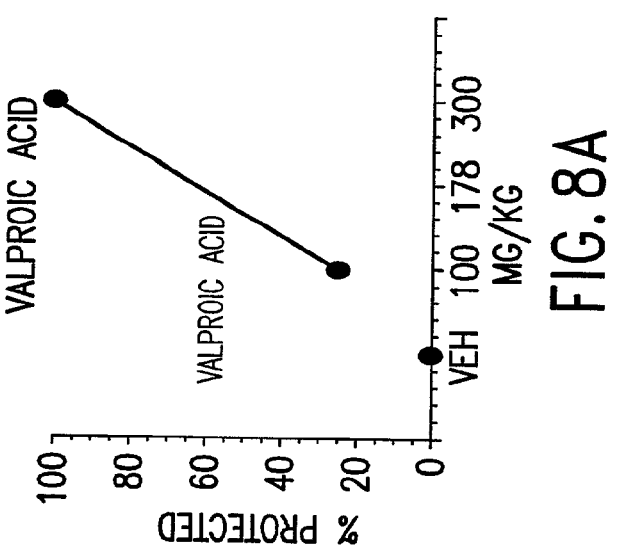

FIG. 8. Protection against pentelenetetrazol-induced seizures in the mouse. Adult male mice were treated with valproic acid (FIG. 8a), Compound A (FIG. 8b), and Compound B (FIG. 8c) at doses from 30–178 mg/kg i.p. (n=8/dose). Thirty minutes later, these animals were challenged with pentelenetetrazol (85 mg/kg, SC) and observed for onset of seizures during a 30 minute test period. The number of animals protected from seizures was plotted versus dose of test compound and ED50s were estimated from this dose-response data.

DESCRIPTION OF THE SEQUENCES

SEQ ID NO:1 is an amino acid sequence containing the intracellular receptor region of the α-subunit of the hKv1.1 protein.

SEQ ID NO:2 is an amino acid sequence containing the intracellular receptor region of the α-subunit of the hKv1.4 protein.

SEQ ID NO:3 is a nucleotide sequence containing the nucleotide sequence encoding the intracellular receptor region of the α-subunit of the hKv1.1 protein.

SEQ ID NO:4 is a nucleotide sequence containing the nucleotide sequence encoding the intracellular receptor region of the α-subunit of the hKv1.4 protein.

SEQ ID NO:5 is an amino acid sequence containing the amino-terminal inactivation region of the hKvβ1 protein.

SEQ ID NO:6 is an amino acid sequence containing the amino-terminal inactivation region of the hKv1.4 protein.

SEQ ID NO:7 is a nucleotide sequence containing the nucleotide sequence encoding the amino-terminal inactivation region of the hKvβ1 protein.

SEQ ID NO:8 is a nucleotide sequence containing the nucleotide sequence encoding the amino-terminal inactivation region of the hKv1.4 protein.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the term "ion channel protein" refers generally to voltage-gated ion channels, including the pore-forming α-subunit proteins ("α-subunits") and the cytoplasmic β-subunit proteins (also known in the art as "auxiliary subunits" or "β-subunits").

The term "intracellular receptor region" means a portion of an α-subunit of a voltage-gated ion channel which can form a specific binding interaction with an amino-terminal portion (i.e., an amino-terminal inactivation region) of an ion channel protein. The term "S4–S5 cytoplasmic receptor domain" refers to the stretch of hydrophilic amino acid residues between the membrane-spanning segments S4 and S5 (also known as "H4") of a pore-forming α-subunit.

The term "amino-terminal inactivation region" means a portion of an ion channel protein which can form a specific binding interaction with an intracellular receptor region of an α-subunit. The amino-terminal inactivation region (also known in the art as the "inactivation gate," "inactivating ball," or "ball peptide") is a globular domain on the amino-terminus of an ion channel protein, including, for example, the globular domain on the amino-terminus of an α-subunit (i.e., linked to the first membrane-spanning segment of an α-subunit) or the amino-terminus of a β-subunit.

As used herein, the term "biologically active fragment" means a portion of an intracellular receptor region or an amino-terminal inactivation region capable of binding to an amino-terminal inactivation region or an intracellular receptor region, respectively. The term "fragment," as applied in this context, will typically be at least about 6 amino acids, usually at least about 8 contiguous amino acids, preferably at least about 10 contiguous amino acids, more preferably at least about 12 contiguous amino acids, and most preferably at least about 14 or more contiguous amino acids in length. Such fragments can be generated by methods known to those skilled in the art, including proteolytic cleavage of the polypeptide, de novo synthesis of the fragment, or genetic engineering.

As used herein, the term "peptide binding pair" means a pair of proteins or polypeptides whose binding interaction results in activation of a signal transduction pathway in a cell or organism. The term "effector molecule" means a peptide or polypeptide that can be expressed as a fusion protein and, when so expressed, can activate an "indicator molecule," provided the effector molecule is translocated to the cell compartment containing the indicator molecule. As used herein, the term "indicator molecule" means a molecule acted upon by the effector molecule, either directly or indirectly through an intermediate molecule, such that activation of the indicator molecule produces a detectable signal. The term "activate" or "activation," when used in reference to an indicator molecule, means that the effector molecule has changed the indicator molecule such that the effector function can be detected as a signal generated by the changed indicator molecule or by a molecule subsequently acted upon by the changed indicator molecule. Various effector molecules and indicator molecules are known in the art, including, for example, the "effector proteins" and "reporter molecules," respectively, described in U.S. Pat. No. 5,776,689 (Karin et al.), which is incorporated by reference in its entirety herein.

The term "cell compartment localization domain" means a peptide or polypeptide sequence that directs translocation of a fusion protein containing the effector molecule to a particular cell compartment. Various cell compartment localization domains are known in the art, including, for example, plasma membrane localization sequences, nuclear localization signal sequences, mitochondrial membrane localization sequences, and the like. See, e.g., Karin et al., supra.

Provided by the present invention are methods and compositions for identifying compounds which affect the binding interaction between two key regulatory regions of voltage-gated ion channels, namely an intracellular receptor region of an α-subunit and an amino-terminal inactivation region of an ion channel protein. The present inventors have discovered that compounds that disrupt binding of these two key regulatory regions have significant modulatory effects on ion channel activity, and thus are expected to be clinically significant therapeutic agents for treating and/or preventing a wide variety of diseases and pathological conditions associated with ion channel dysfunction. Such compounds may also be useful as commercial or biological research reagents, for example, to further define interaction domains of ion channel proteins. Surprisingly, compounds identified using the methods of the invention have been found to selectively and dose-dependently eliminate "N-type" ion channel inactivation (discussed below) in modified host cells expressing these heterologous regulatory regions. Also surprisingly, these compounds exhibit potent anti-seizure activity both in vitro and in vivo. Thus, the present invention represents a significant advance in the pharmacological and pharmaceutical arts, by providing a reliable high-throughput screen which can identify potent and selective modulators of N-type inactivation of voltage-gated ion channels.

As discussed above, voltage-gated ion channels, and particularly potassium and sodium channels, are important determinants of membrane excitability. Each of these families of ion channels comprise several classes of proteins, including the pore-forming α-subunits and the auxiliary β-subunits. The α-subunits comprise six transmembrane-spanning regions, usually referred to sequentially as S1 through S6. The sequences between segments S4 and S5, the "S4–S5 region," and sequences of segment S6 form part of the inner mouth and pore of ion channels, whereas part of the H5 region forms part of the outer mouth and outer half of the pore. See Heinemann, S., et al., *J. Physiol.* 88:173–180 (1994); Durrell, S. R. and R. Guy, *Biophys. J.* 62:238–250 (1992). Segment S4 contains several positively charged amino acids and is believed to be the voltage-sensing α helix. The amino-terminal domain of ion channels is involved in subunit assembly and channel inactivation. Li, M., et al., *Science* 257:1225–1230 (1992); Hoshi, T., et al., *Science* 250:533–538 (1990). Rapidly inactivating A-type ion channels have an amino-terminal inactivation domain which is able to close the open channel from the inside at depolarized membrane potentials, as will be discussed more fully below. This type of inactivation is often referred to as "N-type" inactivation. Hoshi, et al., supra.

N-type inactivation operates in a ball-and-chain type mechanism. Hoshi, et al., supra; Zagotta, W. N., et al., *Science* 250:568–570 (1990). The amino terminus of the α-subunit is the "ball" which swings into the open pore, binds to a receptor site (the intracellular receptor region) and thereby plugs the ion channel pore. This mechanism has been confirmed by several researchers. Mutations within the amino-terminal ball or a deletion of this ball abolishes rapid N-type inactivation. Also, mutations within the S4–S5 region disrupt N-type inactivation. Isacoff, E. Y., et al., *Nature* 353:86–90 (1991). The on-rate time constant for binding the inactivating domain to the receptor is voltage-dependent, such that depolarization of the membrane accelerates the binding. Conversely, the off-rate time constant is also voltage-dependent, but is significantly faster at negative than at more positive membrane potentials. S. Heinemann, supra; Ruppersberg, J. P., et al., *Nature* 353:657–660 (1991). Upon depolarization, the ball moves into the electric field of the membrane and obstructs the open channel pore. Upon repolarization of the membrane the off-rate is faster than the on-rate time constant. This causes the ball to swing away from the ion channel pore and to free the ion channel from inactivation. Thus, the ratio between on- and off-rate at negative membrane potentials may also be an important determinant for the refactory period which A-type ion channels require for recovery from inactivation. S. Heinemann, supra.

As described above for α-subunits, the amino terminus of β-subunits also functions as a tethered inactivating ball which swings into the inner mouth of the ion channels and occludes the pore upon depolarization of the membrane. The amino terminus of β-subunits has been shown to be structurally and functionally similar to the inactivating ball domain of α-subunits. S. Heinemann, supra. A hallmark of the inactivating domain of both α and β-subunits is the presence of an amino terminal cysteine followed by a cluster of positively charged amino acids (lysines and arginines). Ruppersberg, et al., supra. The latter may be important for moving the inactivating ball into the electric field, the cysteine for interaction with the intracellular receptor region at or near the entrance of the ion channel pore. S. Heinemann, supra.

In one aspect, the invention provides methods for detecting a compound that inhibits binding of an intracellular receptor region of an α-subunit and an amino-terminal inactivation region of an ion channel protein, thereby keeping rapidly inactivating channels open longer. The methods comprise contacting the compound with the intracellular receptor region and the amino-terminal inactivation region, and determining the ability of the compound to interfere with the functional interaction or binding of these two regions. A decrease in binding in the presence of the compound compared to the binding in the absence of the compound indicates that the compound inhibits binding interaction between these two regulatory regions. Although this method will work using any appropriately constructed in vitro or in vivo system which allows monitoring of these specific interactions, the invention is preferably practiced using a modified host cell which expresses these heterologous regulatory regions, such as the two-hybrid system described below. The method is generally applicable to voltage-gated ion channels which inactivate via an N-type inactivation mechanism, and particularly voltage-gated potassium and sodium ion channels.

In one embodiment, the method comprises adding a candidate compound to a modified host cell and comparing the exhibition of a selected phenotype in the presence and absence of the compound, wherein the modified host cell is adapted to exhibit a change in phenotype only in the presence of a molecule which inhibits the binding of the intracellular receptor region to the amino-terminal inactivation region. Preferably, the modified host cell comprises an inverse selection (also known as "counter" or "rescue") "two-hybrid" system, such as the modified yeast two-hybrid screen described herein.

In another aspect, the invention provides modified host cells which are useful for screening candidate compounds for ion channel modulatory activity. In a preferred embodiment, the modified host cell comprises a first hybrid protein comprising a DNA-binding domain of a transcriptional activator in polypeptide linkage to either (i) an intracellular receptor region of an α-subunit of a voltage-gated ion channel or (ii) an amino-terminal inactivation region of an ion channel protein, and a second hybrid protein comprising an activation domain of a transcriptional activator in polypeptide linkage to the intracellular receptor region if the DNA-binding domain is in polypeptide linkage to the amino-terminal inactivation region or to the amino-terminal inactivation region if the DNA-binding domain is in polypeptide linkage to the intracellular receptor region.

The intracellular receptor region of the α-subunit of a voltage-gated ion channel, for purposes of the present invention, are those regions of the α-subunit that bind to the amino-terminal inactivation region of an ion channel protein. By way of example, the amino acid sequences for the intracellular receptor regions of certain α-subunits are set forth herein in FIG. 1. These sequences can be easily identified in any α-subunit of a voltage-gated ion channel given the high degree of homology among these sequences. In the example of FIG. 1, the intracellular receptor regions ("loops") of the human Kv1.2 ("hKv1.2"), human Kv1.3 ("hKv1.3"), human Kv1.4 ("hKv1.4"), human Kv1.5 ("hKv1.5"), human Kv1.6 ("hKv1.6") and human Kv3.4 ("hKv3.4") are shown in alignment with human Kv1.1 ("hKv1.1"). [As used herein and consistent with art-recognized usage, "Kv" refers to a voltage-gated potassium ion channel protein.] It is expected that intracellular receptor regions of currently unidentified α-subunits will contain a homology of at least 60%, preferably at least 75%, more preferably at least 85%, and most preferably at least 90 to 95%, based on the homologies present in the α-subunits of the hKv1 and hKv3 channel proteins. Due to the high degree of conservation of sequences among all known α-subunits of voltage-gated ion channels, additional members of the potassium channel family, as well as members of the sodium channel family, are expected to comprise intracellular receptor regions which are structurally and functionally equivalent to those of the hKv1.1 and hKv1.4 α-subunits exemplified in the Examples hereof. Thus, the general features contained and described herein will be applicable to newly discovered ion channel proteins.

The amino-terminal inactivation region of an ion channel protein, for purposes of the present invention, are those regions of the ion channel protein that bind to the intracellular receptor region of an α-subunit. By way of example, the amino acid sequences for the amino-terminal inactivation regions of certain ion channel proteins are set forth herein in FIG. 2. In the example of FIG. 2, the amino-terminal inactivation regions of human Kvβ1b ("Kvβ1b"; also known as "Kvβ1.2"), human Kvβ1c ("Kvβ1c"; also known as "Kvβ1.3"), Kvβ3 ("Kvβ3"), human Kv1.4 ("Kv1.4"), and human Kv3.4 ("Kv3.4") are shown in alignment with human Kvβ1 ("Kvβ1"). As can be seen in this figure, the amino-terminal inactivation regions in each of these subunits can be readily identified by the presence of an amino terminal cysteine residue connected to a string of positively charged amino acids (i.e., lysines and arginines). It is expected that amino-terminal inactivation regions of currently unidentified ion channel proteins will contain a homology of at least 60%, preferably of at least 75%, more preferably at least 85%, and most preferably at least 90 to 95%, based on the homologies present in the amino-terminal inactivation regions of the Kvβ1, Kvβ1.2, Kvβ1.3, Kvβ3, Kv1.4, and Kv3.4 channel proteins. Due to the characteristic chemical composition and structure of the globular domain on the amino-terminus of ion channel proteins, additional members of the potassium channel family, as well as members of the sodium channel family, are expected to comprise amino-terminal activation regions which are structurally and functionally equivalent to those of the hKvβ1 and hKv1.4 subunits exemplified in the Examples hereof. Thus, the general features contained and described herein will be applicable to newly discovered ion channel proteins.

In preferred embodiments, the voltage-gated ion channel is a potassium or sodium channel, the intracellular receptor region is an S4–S5 cytoplasmic receptor domain of an α-subunit or a biologically active fragment thereof, and the amino-terminal inactivation region is the amino-terminal domain of an α- or β-subunit of a potassium or sodium channel protein, or a biologically active fragment thereof. Preferably, the intracellular receptor region comprises the S4–S5 cytoplasmic receptor domain of a potassium channel protein selected from the group consisting of Kv1.1, Kv1.4, and Kv3.4, and the amino-terminal inactivation region comprises the amino-terminal inactivation domain of a potassium channel protein selected from the group consisting of Kvβ1, Kvβ1.2, Kvβ1.3, Kvβ3, Kv1.4, and Kv3.4. In particularly preferred embodiments, the intracellular receptor region has an amino acid sequence as set forth in SEQUENCE (SEQ) ID NO:1 (GenBank Accession No. L02750) and SEQ ID NO:2 (GenBank Accession No. M55514), as well as DNA sequences encoding these sequences, such as the sequences shown in SEQ ID NO:3 (GenBank Accession No. L02750) and SEQ ID NO:4 (GenBank Accession No. M55514), and the amino-terminal inactivation region has an amino acid sequence as set forth in SEQ ID NO:5 (GenBank Accession No. X83127) and SEQ ID NO:6 (GenBank Accession No. L02751), as well as DNA sequences encoding these sequences, such as the sequences shown in SEQ ID NO:7 (GenBank Accession No. X83127) and SEQ ID NO:8 (GenBank Accession No. L02751). Also included are naturally occurring allelic sequences of SEQ ID NO:3, 4, 7 and 8, and equivalent degenerative codon sequences of the above.

The invention further provides methods for detecting a compound that inhibits binding of an intracellular receptor region of an α-subunit and an amino-terminal inactivation region of an ion channel protein utilizing an improved two-hybrid system, such as the yeast two-hybrid screen exemplified herein. The yeast two-hybrid screen is generally known in the art. See, e.g. Fields, et al., *Nature* 340:245–246 (1989), and as modified by Young, K. H. and B. A. Ozenberger in PCT WO 95/34646 (Dec. 21, 1995), the whole of which is incorporated by reference herein. The present invention provides an improved two-hybrid system by utilizing two vectors which have not heretofore been utilized in such a system. In particular, the present invention provides an improved two-hybrid system, wherein the improvement comprises a first vector containing nucleic acid sequences encoding a fusion protein of a DNA binding domain of a transcriptional activator and either (i) an intracellular receptor region of an α-subunit of a voltage-gated ion channel or (ii) an amino-terminal inactivation region of an ion channel protein, and a second vector containing nucleic acid sequences encoding a fusion protein of an activation domain of a transcriptional activator and the intracellular receptor region if the first vector encodes a fusion protein comprising the amino-terminal inactivation region or to the amino-terminal inactivation region if the first vector encodes a fusion protein comprising the intracellular receptor region. As will be appreciated by those skilled in this art, the expression of the DNA binding fusion protein and the activation fusion protein can be interchanged, such that the intracellular receptor region is expressed as a fusion with either the transcription DNA binding domain or the activation domain of the transcriptional activator.

Briefly, using a two-hybrid system, a candidate compound is introduced into the system (a host cell), and a change in a reporter or marker protein product is assayed. Any compound which alters the level of expression of the reporter or marker, as monitored by a suitable assay, is a potential drug candidate and may be suitable for further, in-depth studies of therapeutic applications. The candidate compound may be of any form suitable for entry into the cytoplasm and/or nucleus of the modified host cell. Under appropriate conditions, the candidate compound may be allowed to freely diffuse into the cell, or the delivery of the compound may be facilitated by techniques and substances which enhance cell permeability, a wide variety of which are known in the art. Methods for increasing cell permeability include, without limitation, the use of organic solvents such as dimethylsulfoxide, hydrolytic enzymes (which degrade cell walls), yeast cell mutants (e.g., erg-), liposomes, application of electrical current, and physical means such as compound-coated teflon pellets.

The host organism ("modified host cell") may be any eukaryotic or prokaryotic cell, or multicellular organism. Many strains of yeast cells known to those skilled in the art may be available as host cells for practicing the present invention. Suitable host cells may also be mammalian cells, such as Chinese hamster ovary cells (CHO), the monkey COS-1 cell line, and the mammalian cell CV-1, or amphibian cells, such as a *Xenopus* egg cell. Bacterial cells may also be suitable hosts. For example, the various strains of *E. coli* (e.g., HB101, MC1061) are well-known as host cells in the field of biotechnology. Various strains of *B. subtillis*, *Pseudomonas*, other bacilli and the like may also be employed in this method. Additionally, where desired, insect cells may be utilized as host cells in the method of the present invention. See, e.g. Miller et al, *Genetic Engineering*, 8:277–298 (Plenum Press 1986) and references cited therein. In preferred embodiments, the modified host cell is a yeast or mammalian cell. More preferably, the modified host cell is a yeast cell selected from the group consisting of *Saccharomyces cerevisiae*, *Schizosaccharomyces pombe*, and *Pichia pastoris*. In a particularly preferred embodiment, the modified host cell is a yeast cell derived from a Saccharomyces organism having the genotype MATa, gal80, gal 4, his3, ade2-101, leu2-3, 112 trp1-901, ura3-52 cyh LYS2::GAL$_{UAS}$-HIS3.

The transcriptional activation protein ("transcriptional activator") may vary widely as long as the DNA binding domains and the activation domains are known or can be deduced by available scientific methods. The transcriptional activator may be any protein having two components, a DNA binding component and an activation component, wherein the transcriptional activator contains an acidic α-helix for the activation of transcription. Preferably, the transcriptional activator is selected from the group consisting of Gal4, Gcn4, Hap1, Adr1, Swi5, Ste12, Mcm1, Yap1, Ace1, Ppr1, Arg81, Lac9, Qa1F, VP16, LexA, non-mammalian nuclear receptors (e.g., ecdysone) or mammalian nuclear receptors (e.g., estrogen, androgens, glucocorticoids, mineralocorticoids, retinoic acid and progesterone). See Picard, D., et al., *Gene* 86:257–261 (1990). Preferably, the transcriptional activator is a yeast protein, and more preferably, the transcriptional yeast protein is Gal4, Gcn4 or Adr1. In general, any DNA binding protein which functions with an activation domain may be used. A DNA binding protein may be substituted for the DNA binding domain of a transcriptional activation protein if the recognition sequences operatively associated with the reporter gene are correspondingly engineered. Illustrative of non-yeast DNA binding proteins are mammalian steroid receptors and bacterial LexA. See Wilson, T. E., et al., *Science* 252:1296–1300 (1990).

The modified host cell may comprise a reporter gene whose transcription is dependent upon binding between the first and second hybrid proteins, thereby reconstituting a transcriptional activator. The reporter gene is generally selected in order that the binding of the domains of the transcriptional activation protein can be monitored by well-known and straightforward techniques. Preferably, the reporter gene is selected based on its cost, ease of measuring its activity, and low background (i.e., the activity can be determined at relatively low levels of expression of the reporter gene because of a high signal to background ratio and/or minimal or no uninduced activity). Suitable reporter genes include, for example, genes which confer a selectable phenotype to cells in which the reporter gene is efficiently expressed, and/or encode a gene product (e.g., enzyme) which is conveniently detected such as by in situ assay, or the like. Illustrative of reporter genes which may be used in the present invention are reporter genes selected from the following: genes which confer sensitivity to a chemical, such as CYH2 (cyclohexamide sensitivity) and CAN1 (canavine); genes which confer resistance to a chemical (e.g., an antibiotic), such as neo$^r$ and KAN; genes which complement auxotrophic mutations in a host organism, such as HIS3, URA3, LEU2, ARG, MET, ADE, LYS, and TRP, and the like; genes which encode toxic gene products, such as ricin; and LACZ, LAC1, firefly luciferase, bacterial luciferase, green fluorescent protein, CAT (chloramphenicol acetyl transferase), alkaline phosphatase, horseradish peroxidase, and the like.

In one embodiment, the present invention may be practiced using a conventional two-hybrid system which relies upon a positive association between two Gal4 fusion proteins, thereby reconstituting a functional Gal4 transcriptional activator which then induces transcription of a reporter gene operably linked to a Gal4 binding site. Transcription of the reporter gene generally produces a positive readout, typically manifested either as an enzyme activity (e.g., β-galactosidase) that can be identified by a calorimetric enzyme assay, or as enhanced cell growth on a defined medium (e.g., HIS3). Using conventional two-hybrid systems, a compound which is capable of inhibiting N-type inactivation of a voltage-gated ion channel is identified by its inhibitory affect on reporter gene expression (e.g., reduced enzyme activity or cell growth).

In a preferred embodiment, the methods of the present invention are practiced using an "inverse" (also known as "counter selection" or "reverse") two-hybrid system. Using an inverse two-hybrid system, compounds which are capable of affecting N-type inactivation of a voltage-gated ion channel will generate a selectable and/or detectable readout (e.g., complementation of an auxotrophic phenotype, expression of a detectable reporter molecule, and the like). Typically, an inverse two-hybrid system produces a positive readout under conditions wherein an agent blocks or otherwise inhibits the intermolecular binding of the interacting polypeptides (i.e., an intracellular receptor region of an α-subunit and an amino-terminal inactivation region of an ion channel protein). A positive readout condition is generally identified as one or more of the following detectable conditions: (1) an increased transcription rate of a reporter gene, (2) an increased concentration or abundance of a polypeptide product encoded by a reporter gene, typically such as an enzyme which can be readily assayed in vivo, and/or (3) a selectable or otherwise identifiable phenotypic change in the organism harboring the inverse two-hybrid system. Generally, a selectable or otherwise identifiable phenotypic change that characterizes a positive readout condition confers upon the organism either a selective growth advantage on a defined medium, drug resistance, a characteristic morphology or developmental stage, or a detectable enzymatic activity (e.g., β-galactosidase, luciferase, alkaline phosphatase, and the like). In this manner, it is possible to efficiently identify agents (including but not limited to small molecules, polypeptides, peptides and oligonucleotides) which inhibit intermolecular binding between an intracellular receptor region of a voltage-gated ion channel and an amino-terminal inactivation region of an ion channel protein.

In another aspect, the invention provides a modified host cell comprising a first hybrid protein comprising an intracellular receptor region of an α-subunit of a voltage-gated ion channel in polypeptide linkage to a first peptide of a peptide binding pair, and a second hybrid protein comprising an amino-terminal inactivation region of an ion channel protein in polypeptide linkage to a second peptide of the peptide binding pair, wherein a functional or binding interaction between the two peptides causes activation of a signal transduction pathway in the modified host cell. In accordance with this aspect of the invention, one of the two peptides of the peptide binding pair is a cell compartment localization domain and the other peptide is an effector molecule. In this aspect of the invention, the activity of an endogenous effector molecule in the host cell is defective due, for example, to a mutation which prevents activation of the indicator molecule, or the effector molecule is expressed at a level that does not produce maximum activation of the indicator molecule. When the two hybrid proteins are expressed in an appropriate host cell, one hybrid protein is localized to the appropriate cell compartment via the cell compartment localization domain (e.g., to the inner surface of the cell membrane via a myristylation tag). Functional interaction between the intracellular receptor region and the amino-terminal inactivation region facilitates activation of an indicator molecule by the effector molecule, wherein activation of the indicator molecule generates a selectable or otherwise identifiable phenotypic change that characterizes a positive readout condition, as described above. In this manner, it is possible to efficiently identify agents which affect intermolecular binding between an intracellular receptor region of a voltage-gated ion channel and an amino-terminal inactivation region of an ion channel protein.

Preferably, the cell compartment localization domain is a plasma membrane localizing domain such as the sequence of v-Src that acts as a myristoylation signal, the sequence of H-Ras that acts as a signal for farnesylation and palmitoylation, or the sequence of K-Ras4B that acts a farnesylation signal. Expression of a fusion protein containing one of these domains results in farnesylation or myristoylation of the fusion protein and localization of the fusion protein or a complex containing the fusion protein to the plasma membrane. In addition, a domain such as a pleckstrin homology domain can be useful for localizing a fusion protein to the plasma membrane. For a description of plasma membrane localizing domains useful in the present invention, see, for example, Buss et al., *Mol. Cell. Biol.* (1988) 8:3960–3963; Karin et al., U.S. Pat. No. 5,776,689; Hancock et al., *EMBO J.* (1991) 10:4033–4039; and Shaw, *BioEssays* (1996) 18:35–46, each of which is incorporated by reference in its entirety herein. See also Broder, Y. C., et al., *Curr. Biol.* (1998) 8(20):1121–1124, and Aronheim, A., et al., *Mol. Cell. Biol.* (1997) 17(6):3094–3102, both of which are incorporated by reference herein.

The effector molecule may be any peptide or polypeptide that can be expressed as a fusion protein and, when so expressed, can activate an indicator molecule. For example, the effector molecule may be an active fragment of an effector protein such as a guanine nucleotide exchange factor ("GEF"), provided the active fragment comprises a sufficient portion of the effector protein so as to confer the effector function. In an exemplified embodiment, the effector molecule is human Sos ("hSos"), which is known to activate Ras. See Chardin et al., *Science* (1993) 260:1338–1343, which is incorporated by reference herein. Activation of Ras by hSos does not require the full length Sos protein, but requires, at a minimum, an active fragment that maintains guanine nucleotide exchange activity and converts Ras-GDP to Ras-GTP. See Aronheim et al., *Cell.* (1994) 78:949–961; Quilliam et al., *Proc. Natl. Acad. Sci. USA* (1994) 91:8512–8516; Lai et al., *Mol. Cell. Biol.* (1993) 13:1345–1352; and Boguski and McCormick, *Nature* (1993) 366:643–654. Such active fragments of an effector protein are considered to be within the meaning of the term "effector molecule" as used herein.

A wide variety of indicator molecules which cause activation of a signaling pathway, and which may be used in the practice of the present invention, are well known and readily available in the art, including, without limitation, G protein-linked receptors and their ligands (e.g., receptors for epinephrine, serotonin, and glucagon, and the like, and their respective ligands); ion-channel receptors and ligands (e.g., acetylcholine receptor and ligand); receptors associated with cytosolic protein tyrosine kinases and their ligands; receptors with intrinsic enzymatic activity and their ligands (e.g., receptor serine/threonine kinases and receptor tyrosine kinases, and their respective ligands); and yeast G protein coupled receptors and their ligands (e.g., yeast phereomone receptors such as STE2 and STE3, whose ligands are alpha-factor or a-factor). Preferably, the indicator molecule is a protein selected from the group consisting of a mitogen-activated protein (MAP) kinase, a MAP kinase related protein, a RAS protein, a RAS related protein, a Janus kinase (JAK), a JAK related protein, a c-Jun N terminal kinase (JNK), a JNK related protein, insulin receptor substrate 1 (IRS-1), and an IRS-1 related protein. The term "related," as applied in this context, refers to a protein or polypeptide having similar biological activity to one of the above-referenced proteins. In particularly preferred embodiments, the first or second peptide of the peptide binding pair is a MAP kinase or a Ras protein. For a description of indicator molecules useful in the present invention, see, for example, Gustin, M. C., et al., *Microbiol. Mol. Biol. Rev.* (1998) 62(4):1264–1300 [MAP kinase]; Force, T. and J. V. Bonventre, *Hypertension* (1998) 31(1):152–161 [MAP kinase]; Carter-Su, C. and L. S. Smit, *Hormone Res.* (1998) 53:61–83 [JAK]; Avruch, J., *Mol. Cell. Biochem.* (1998) 182(1–2): 31–48 [IRS-1]; Whitmarsh, A. J. and R. J. Davis, *J. Mol. Med.* (1996) 74(10):589–607 [JNK and MAP kinase]; Karin et al., U.S. Pat. No. 5,776,689; and Aronheim, supra, each of which is incorporated by reference in its entirety herein.

The invention includes polynucleotides, expression vectors, and host cells transfected or transformed with expression vectors containing nucleotide sequences which encode an intracellular receptor region of an α-subunit of a voltage-gated ion channel and an amino-terminal inactivation region of an ion channel protein, or biologically active fragments thereof.

The modified host cells of the present invention comprise hybrid proteins containing polypeptides (i.e., intracellular receptor regions and amino-terminal inactivation regions) or fragments thereof having amino acid sequence lengths that are at least 25% (more preferably at least 50%, and most preferably at least 75%) of the length of a disclosed polypeptide (i.e., a polypeptide having an amino acid sequence as set forth in SEQ ID NO:1, SEQ ID NO:2, SEQ ID NO:5, or SEQ ID NO:6), and have at least 60% sequence identity (preferably at least 75% identity; more preferably at least 85%, and most preferably at least 90% to 95% identity) with that disclosed polypeptide, where sequence identity is determined by comparing the amino acid sequences of the polypeptides when aligned so as to maximize overlap and identity while minimizing sequence gaps. Also included in the present invention are polypeptides and fragments thereof that contain a segment comprising 6 or more (preferably 8 or more, more preferably 10 or more, and most preferably 12 or more) contiguous amino acids that shares at least 60% sequence identity (preferably at least 75% identity, more preferably at least 85% identity; and most preferably at least 90% to 95% identity) with any such segment of any of the disclosed polypeptides.

In particular, sequence identity may be determined using WU-BLAST (Washington University BLAST) version 2.0 software, which builds upon WU-BLAST version 1.4, which in turn is based on the public domain NCBI-BLAST version 1.4 (Altschul and Gish, Local alignment statistics, Doolittle ed., *Methods in Enzymology* 266:460–480 (1996); Altschul et al., Basic local alignment search tool, *Journal of Molecular Biology* 215:403–410 (1990); Gish and States, Identification of protein coding regions by database similarity search, *Nature Genetics* 3:266–272 (1993); Karlin and Altschul, Applications and statistics for multiple high-scoring segments in molecular sequences, *Proc. Natl. Acad. Sci. USA* 90:5873–5877 (1993); all of which are incorporated by reference herein). WU-BLAST version 2.0 executable programs for several UNIX platforms can be downloaded from ftp://blast.wustl.edu/blast/executables. The complete suite of search programs (BLASTP, BLASTN, BLASTX, TBLASTN, and TBLASTX) is provided at that site, in addition to several support programs. WU-BLAST 2.0 is copyrighted and may not be sold or redistributed in any form or manner without the express written consent of the author; but the posted executables may otherwise be freely used for commercial, nonprofit, or academic purposes. In all search programs in the suite—BLASTP, BLASTN, BLASTX, TBLASTN and TBLASTX—the gapped alignment routines are integral to the database search itself, and thus yield much better sensitivity and selectivity while producing the more easily interpreted output. Gapping can optionally be turned off in all of these programs, if desired. The default penalty (Q) for a gap of length one is Q=9 for proteins and BLASTP, and Q=10 for BLASTN, but may be changed to any integer value including zero, one through eight, nine, ten, eleven, twelve through twenty, twenty-one through fifty, fifty-one through one hundred, etc. The default per-residue penalty for extending a gap (R) is R=2 for proteins and BLASTP, and R=10 for BLASTN, but may be changed to any integer value including zero, one, two, three, four, five, six, seven, eight, nine, ten, eleven, twelve through twenty, twenty-one through fifty, fifty-one through one hundred, etc. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

The present invention also includes polynucleotides that hybridize under reduced stringency conditions, more preferably stringent conditions, and most preferably highly stringent conditions, to polynucleotides described herein (i.e., the polynucleotides as depicted in SEQ ID NO:3, SEQ ID NO:4, SEQ ID NO:7, or SEQ ID NO:8). Examples of stringency conditions are shown in the table below: highly stringent conditions are those that are at least as stringent as, for example, conditions A–F; stringent conditions are at least as stringent as, for example, conditions G–L; and reduced stringency conditions are at least as stringent as, for example, conditions M–R.

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≧50 | 65° C.; 1 × SSC -or- 42° C.; 1 × SSC, 50% formamide | 65° C.; 0.3 × SSC |
| B | DNA:DNA | <50 | $T_B$*; 1 × SSC | $T_B$*; 1 × SSC |
| C | DNA:RNA | ≧50 | 67° C.; 1 × SSC -or- 45° C.; 1 × SSC, 50% formamide | 67° C.; 0.3 × SSC |
| D | DNA:RNA | <50 | $T_D$*; 1 × SSC | $T_D$*; 1 × SSC |
| E | RNA:RNA | ≧50 | 70° C.; 1 × SSC -or- 50° C.; 1 × SSC, 50% formamide | 70° C.; 0.3 × SSC |
| F | RNA:RNA | <50 | $T_F$*; 1 × SSC | $T_F$*; 1 × SSC |
| G | DNA:DNA | ≧50 | 65° C.; 4 × SSC -or- 42° C.; 4 × SSC, 50% formamide | 65° C.; 1 × SSC |
| H | DNA:DNA | <50 | $T_H$*; 4 × SSC | $T_H$*; 4 × SSC |
| I | DNA:RNA | ≧50 | 67° C.; 4 × SSC -or- 45° C.; 4 × SSC, 50% formamide | 67° C.; 1 × SSC |
| J | DNA:RNA | <50 | $T_J$*; 4 × SSC | $T_J$*; 4 × SSC |
| K | RNA:RNA | ≧50 | 70° C.; 4 × SSC -or- 50° C.; 4 × SSC, 50% formamide | 67° C.; 1 × SSC |
| L | RNA:RNA | <50 | $T_L$*; 2 × SSC | $T_L$*; 2 × SSC |
| M | DNA:DNA | ≧50 | 50° C.; 4 × SSC -or- 40° C.; 6 × SSC, 50% formamide | 50° C.; 2 × SSC |
| N | DNA:DNA | <50 | $T_N$*; 6 × SSC | $T_N$*; 6 × SSC |
| O | DNA:RNA | ≧50 | 55° C.; 4 × SSC -or- 42° C.; 6 × SSC, 50% formamide | 55° C.; 2 × SSC |

-continued

| Stringency Condition | Polynucleotide Hybrid | Hybrid Length (bp)‡ | Hybridization Temperature and Buffer† | Wash Temperature and Buffer† |
|---|---|---|---|---|
| P | DNA:RNA | <50 | $T_P$*; 6 × SSC | $T_P$*; 6 × SSC |
| Q | RNA:RNA | ≧50 | 60° C.; 4 × SSC -or- 45° C.; 6 × SSC, 50% formamide | 60° C.; 2 × SSC |
| R | RNA:RNA | <50 | $T_R$*; 4 × SSC | $T_R$*; 4 × SSC |

‡: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
†: SSPE (1 × SSPE is 0.15M NaCl, 10 mM $NaH_2PO_4$, and 1.25 mM EDTA, pH 7.4) can be substituted for SSC (1 × SSC is 0.15M NaCl and 15 mM sodium citrate) in the hybridization and wash buffers; washes are performed for 15 minutes after hybridization is complete.
*$T_B$–$T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) =81.5 + 16.6($\log_{10}[Na^+]$) + 0.41(% G + C) – (600/N), where N is the number of bases in the hybrid, and [$Na^+$] is the concentration of sodium ions in the hybridization buffer ([$Na^+$] for 1 × SSC = 0.165 M).

Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3–6.4, incorporated herein by reference.

Preferably, each such hybridizing polynucleotide has a length that is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

A further aspect of the invention includes vectors comprising a DNA sequence as described above in operative association with an expression control sequence. Regulatory sequences for such vectors are known to those skilled in the art and may be selected depending upon the host cells. Such selection is routine and does not form part of the present invention. These vectors may be employed in a novel process of the present invention in which a cell line transformed with a DNA sequence encoding an intracellular receptor region and an amino-terminal inactivation region, or biologically active fragments thereof, in operative association with an expression control sequence, is cultured under suitable conditions for growth. The resulting modified host cells are placed in a growth medium, which optionally contains agar, with the test sample applied to the surface of the growth medium. The growth medium is preferably a conventional liquid medium of growth reagents and water, such as yeast synthetic medium (YSM available from BIO101 (also see Rose et al., *Methods in Yeast Genetics*, 1990). As discussed above, this process may employ a number of known cells both prokaryotic and eukaryotic as host cells for expression of the polypeptide.

In order to illustrate the invention, description of preferred embodiments are presented below. One embodiment comprises an inverse two-hybrid system in heterologous yeast cells comprising the interacting components of the human Kv1.1 channel and Kvβ1 which are expressed as fusion proteins to the DNA binding domain or the activation domain, respectively, of the yeast Gal4 transcription activation protein. The expression plasmids were transfected into a host strain which contains an operatively linked CYH2 counter-selection reporter gene. Functional interaction of the Kv1.1 and Kvβ1 domains reconstitutes the function of the yeast Gal4 protein, drives expression of the downstream reporter gene and results in attenuation of yeast cell growth on selective media. Disruption, or blocking, of the interaction between Kv1.1 and Kvβ1 fusion proteins prevents the functional reconstitution of the yeast Gal4 protein, the reporter gene is not activated, and permissive yeast cell growth on selective media (rescue) is observed. A second embodiment comprises a non-transcription based two-hybrid system in heterologous yeast cells comprising the interacting components of the human Kv1.1 channel and Kvβ1 which are expressed as fusion proteins to the C-terminally truncated human SOS (hSOS) or the human myristoylation (hMyr) signal, respectively. The expression plasmids are transfected into a host strain which expresses a temperature sensitive cdc25 gene product. Functional interaction of the Kv1.1 and Kvβ1 domains results in recruitment of the complex to the plasma membrane, allowing growth at the nonpermissive temperature. Disruption of the interaction between Kv1.1 and Kvβ1 fusion proteins prevents the SOS-mediated rescue of the temperature sensitive cdc25 allele, thereby inhibiting yeast cell growth at the nonpermissive temperature A variety of alternative embodiments and variations will be apparent to those of skill in the art, including alternative host cells (e.g., mammalian, bacterial, fungal, insect, and the like), alternative reporter genes, variations of the basic inverse two-hybrid method, variations of the peptide binding pair, alternative indicator molecules, and others. Moreover, in addition to high-throughput screening for potential modulators (both inhibitors and agonists) of N-type ion channel inactivation, the present invention is susceptible to a number of additional uses, such as to further define interaction domains of ion channel proteins, to characterize analogs, and to evaluate candidate compounds generated in structure-activity-relationship programs or using combinatorial chemistry. These variations, modifications, and additional applications constitute part of the present invention.

EXAMPLES

Example 1

Construction of Recombinant Plasmids

Molecular Reagents: Generation of recombinant plasmids employed standard molecular techniques. Oligonucleotides were prepared on an ABI automated synthesizer (Perkin Elmer Cetus, Norwalk, Conn.) with specific sequences detailed below. Polymerase chain reactions (PCR) employed standard techniques (Finney M., *Current Protocols in Molecular Biology*, Wiley & Sons, NY, 1993). In general, PCR products were cloned into pCRII (Invitrogen, Carlsbad, Calif. 92008) as an interim step for PCR product sequence confirmation and propagation for further cloning. The pCRII recombinant plasmids were transfected into OneShot competent *E. coli* cells (Invitrogen, Carlsbad, Calif. 92008), and other recombinant plasmids were transfected into DH5α competent *E. coli* cells (GIBCO Life Technologies, Rockville, Md. 20849), following manufacturer's instructions. Recombinant plasmid stocks were prepared using Qiagen Mini preps (Qiagen, Valencia, Calif.). DNA sequencing was performed using dye-deoxy terminator reactions (Perkin Elmer Cetus, Norwalk, Conn.) and an ABI 373 automated sequencer (Applied Biosystems, Foster City, Calif.).

A. Kv1.1/Kvβ1 Channel Molecular Reagents:

Kv 1.1 alpha S4–5 loop: The cDNA encoding the intracellular loop between the S4 and S5 transmembrane domains of the Kv1.1 potassium channel alpha subunit was generated as oligonucleotides. A 59 base sense oligonucleotide was generated with a 5' precut NcoI site, a stop codon and a 3' precut BamHI site which has the following sequence:

```
5'-C ATG GAG CTC TTC ATC GGG GTC ATC CTG TTT TCT AGT GCA GTG TAC TTT GCC GAG TAA G-3'    [SEQ. ID NO:9]
``` and a 59 base reverse complement oligonucleotide containing a 5' precut BamHI site, a stop codon, and a 3' precut NcoI site which has the following sequence:

```
5'-GA TCC TTA CTC GGC AAA GTA CAC TGC ACT AGA AAA CAG GAT GAC CCC GAT GAA GAG CTC-3'    [SEQ. ID NO:10]
```

The oligonucleotides were phosphorylated and annealed by standard techniques (Manniatus, T., Fritsch, E. F., and Sambrook, J., *Molecular Cloning*, Cold Spring Harbor Laboratory Press, Cold Spring Harbor, N.Y., 1982) and cloned into NcoI-BamHI sites of pAS1 (2 micron plasmid) (Durfee, T., et al., *Gene Devel.* (1993) 7:555–569) to generated S45-pAS1 and cloned into the NcoI-BamHI sites of pUN30AS (CEN plasmid) to generate S45-pUN30AS. See Young, K. H. and B. A. Ozenberger, PCT WO 95/34646 (Dec. 21, 1995); and Young, K. H., et al., *Nature Biotechnology* (1998) 16:946–950, both of which are incorporated by reference in their entireties herein. Both plasmids express the S4–5 loop as a 3' fusion to the yeast Gal4 DNA binding domain protein. Confirmation and orientation of the insert was confirmed by dye deoxy terminator sequence analysis using an ABI 373 automated sequencer (Perkin Elmer Cetus, Norwalk, Conn.).

Kvβ1 full length: The cDNA encoding the full length β1 cytoplasmic protein was generated by PCR using a 55 base sense oligonucleotide containing 5' EcoRI and NdeI restriction sites having the following sequence:

```
5'-C CGA ATT CGA CAT ATG AAA ATG CAA GTC TCC ATA GCC TGC ACA GAG CAC AAT TTG-3'    [SEQ. ID NO:11]
``` and a 42 base antisense oligonucleotide containing a stop codon, EcoRI and BamHI restriction sites having the following sequence:

```
5'-ACG GAT CCC CGA ATT CCA TTA TGA TCT ATA GTC CTT CTT GCT-3'    [SEQ. ID NO:12]
``` and human Kvβ1 as template (GenBank Accession No. U33428). The 1205 bp PCR product encodes bp 28–1233 of human Kvβ1. The cDNA encoding Kvβ1 was cloned into the EcoRI site of pUN100ACT (Young and Ozenberger, PCT WO 95/34646; and Young, et al. (1998), supra), as a 3' fusion to the yeast Gal4 activation domain cDNA and generated recombinant plasmid Kvβ1-pUN100ACT.

Kvβ1 1–100 amino acids: The cDNA encoding amino acids 1–100 of the Kvβ1 subunit which contains the ball peptide inactivation domain was generated by PCR. The 5' oligonucleotide described for the cloning of the full length β1 protein was used in conjunction with a 45 base antisense oligonucleotide containing a stop codon and EcoRI and BamHI restriction sites having the following sequence:

```
5'-ACG GAT CCC CGA ATT CCA TTA ATC TGA AAT TTG ACC TCC AAA TGT-3'    [SEQ. ID NO:13]
``` and human Kvβ1 as template (GenBank Accession U33428). The cDNA encoding β1 1–100 was obtained as an EcoRI fragment and cloned in the EcoRI site of pACT2 (Clontech, Palo Alto, Calif. 94303) to generate β1 1–100-pACT2, as well as cloned into the EcoRI site of pUN100ACT to generate β1 1–100-pUN100ACT. Both recombinant plasmids generate Kvβ1 1–100 as a 3' fusion to the yeast Gal4 activation domain.

B. Kv1.4 Molecular Channel Reagents:

Kv1.4 channel Molecular Reagents: The cDNA encoding the intracellular loop between the S4 and S5 transmembrane regions of the human Kv1.4 subunit (GenBank accession M55514) was generated using a 59 base sense oligonucleotide containing a 5' precut NcoI site, and a 3' stop codon and precut BamHI site having the following sequence:

5'-C ATG GAG CAG ATC CTG GGC CAC ACC CTG AGA GCC AGC ATG CGG GAA CTG GGC CTT TAA G-3' [SEQ. ID NO:14]

and a 59 base reverse complement oligonucleotide having the following sequence:

5'-GA TCC TTA AAG GCC CAG TTC CGG CAT GCT GGC TCT GAG GGT GTG GCC CAG GAT CTG CTC-3' [SEQ. ID NO:15]

The oligonucleotides were phosphorylated and annealed by standard techniques (Manniatus et al., 1982, supra) and directionally cloned into the NcoI-BamHI sites of pAS1 to generate S4–S5 loop# 105-pAS1. The amino terminal region of the human Kv1.4 channel containing the inactivation ball peptide region was generated by PCR using a 60 base sense oligonucleotide containing EcoRI, BamHI, NdeI sites, and a start codon having the following sequence:

5'-CGA ATT CAT ATG CGG ATC CGT AGA ATG GAG GTT GCA ATG GTG AGT GCG GAG AGC TCA GGG-3' [SEQ. ID NO:16]

and a 41 base antisense oligonucleotide containing a stop codon followed by EcoRI and SalI restriction sites having the following sequence:

5'-GGT CGA CGA ATT CGT TAC CTT GCA GGA TCG GAG CTC TCG TG-3' [SEQ. ID NO:17]

and using a human the Kv1.4 clone (GenBank accession M55514) H3MV226str.seq as template. A 950 bp PCR product was generated encoding approximately the first 307 amino acids of the human Kv1.4 alpha subunit. This domain was obtained as a BamHI-SalI fragment from pCRII and subcloned into the BamHI-XhoI site of pACT2 to generate Nfull#49-pACT2.

Kv1.4 EΔQ mutation in S4–5 loop region: A mutated version of the human Kv1.4 S4–5 loop containing a Glu substitution for Gln at amino acid position 395 (Isacoff, E. Y., et al., Nature 353:86–90 (1991)) was generated using a 59 base sense oligonucleotide containing a 5' precut NcoI site, and a stop codon, and a 3' precut BamHI site having the following sequence:

and a 59 base reverse complement oligonucleotide containing a 5' precut BamHI site, a 3' stop codon, and precut NcoI site having the following sequence:

5'-GA TCC TTA AAG GCC CAG TTG CCG CAT GCT GGC TCT GAG GGT GTG GCC CAG GAT CTG CTC-3' [SEQ. ID NO:19]

The oligonucleotides were phosphorylated and annealed by standard techniques (Manniatus et al., 1982, supra) and directionally cloned into the NcoI-BamHI sites of pAS1 to generate EΔQS45-pAS1.

Example 2

Construction of Yeast Strains

A. Generation of Kv1.1/Kvβ1 Yeast Strains:

All strains were generated by transforming expression plasmids into CY770 (Ozenberger and Young, 1995, supra) using the lithium chloride method and grown on synthetic drop-out media to maintain plasmids (Rose, M. D., et al., Methods in Yeast Genetics, Cold Spring Harbor Laboratory Press, Cold Spring Harbor, N.Y., 1990). 3-amino-1,2,4-triazole was used to counteract background expression of the $GAL_{UAS}$-HIS3 reporter. All strains contained a $UAS_{GAL}$-CYH2 reporter plasmids with the following combination of plasmids:

S45-pUN30AS and β1-pUN100ACT (strain YKY4/Kv1.1)
S45-pUN30AS and pUN100ACT (strain YKY15/Kv1.1)
pUN30AS and β1-pUN100ACT (strain YKY16/Kv1.1)
SNF1-pAS1 and SNF4-pACT (strain CY856)
S45-pUN30AS and SNF4-pACT (strain YKY2/Kv1.1)
SNF1-pAS and β1-pUN100ACT (strain YKY5/Kv1.1)
pUN30AS and β1 1–100-pUN100ACT (strain YKY17/Kv1.1)
S45-pUN30AS and pUN100ACT (strain YKY15/Kv1.1)

5'-C ATG GAG CAG ATC CTG GGC CAC ACC CTC AGA GCC AGC ATG CGG CAA CTG GGC CTT TAA G-3' [SEQ. ID NO:18]

B. Generation of Kv1.4 Yeast Strains:

All strains were generated by transforming expression plasmids into CY770 (Ozenberger and Young, 1995, supra) using the lithium chloride method and grown on synthetic drop-out media to maintain plasmids (Rose et al., supra). 3-amino 1,2,4-triazole was used to counteract background expression of the $GAL_{UAS}$-HIS3 reporter. All strains contained a ura marked third plasmid, pCUP (Ozenberger and Young, 1995, supra) and the following combination of plasmids:
S45#105-pAS and Nfull#49-pACT2 (strain YKY15a/Kv1.4)
S45#105-pAS and SNF4-pACT (strain YKY17a/Kv1.4)
SNF1-pAS1 and Nfull#49-pACT2 (strain YKY19/Kv1.4)
SNF1-pAS1 and SNF4-pACT (strain CY856)
EΔQS45-pAS1 and Nfull#49-pACT2 (strain YKY/Kv1.4)

Example 3

Yeast Two-Hybrid Screen

A. Kv1.1/β1 Yeast Two-Hybrid Screen:

The interacting components of the human Kv1.1 channel and Kvβ1 were expressed as fusion proteins to the DNA binding domain or the activation domain, respectively, of the yeast Gal4 transcription activation protein. The expression plasmids were transfected into a host strain which contains a counter selection reporter gene. Functional interaction of the Kv1.1 and Kvβ1 domains reconstitutes the function of the yeast Gal4 protein, drives expression of the downstream reporter gene and results in attenuation of yeast cell growth on selective media. Disruption, or blocking, of the interaction between Kv1.1 and Kvβ1 fusion proteins, prevents the functional reconstitution of the yeast Gal4 protein, the reporter gene is not activated, and permissive yeast cell growth on selective media (rescue) is observed.

Figure 5:
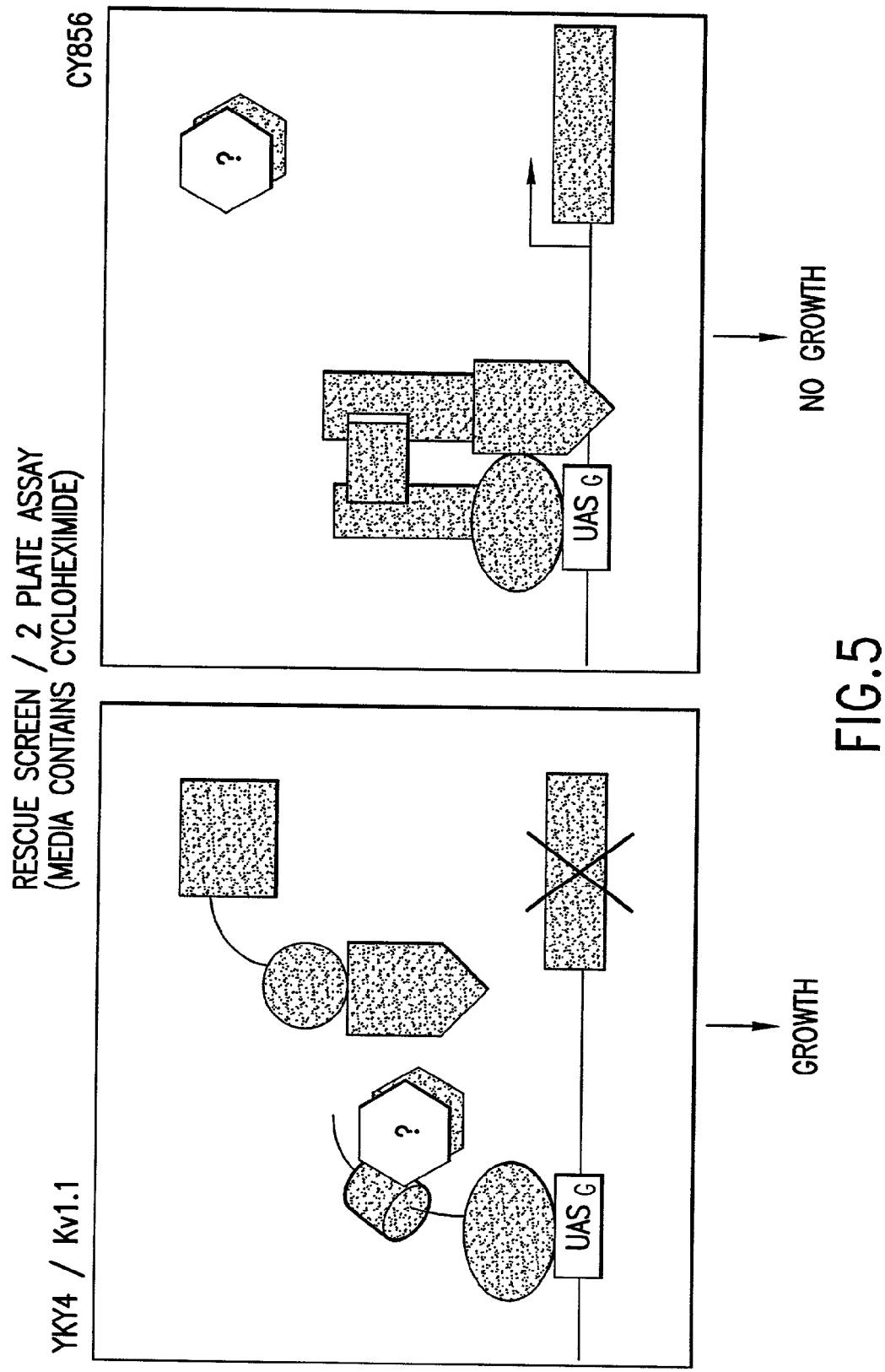

B. Bioassay Conditions:

The N-terminal 307 amino acids of the human Kv1.4 (hKv1.4) α-subunit and the S4–S5 cytoplasmic loop of human Kv1.4 (amino acids 382–398; GenBank M05514) were expressed as fusion partners. As shown in FIG. 3, these two channel domains interact strongly in the yeast two-hybrid system. We then generated yeast constructs expressing either amino-acids 1–100 or the full-length (401 amino acids) hKvβ1 polypeptide together with the S4–S5 loop from hKv1.1 (amino acids 313–328: GenBank accession no. L02750). Both β-subunit constructs interacted with the Kv1.1 S4—S4 loop (FIG. 4); however, the interaction using the full-length Kvβ1 was more robust as measured qualitatively by induction of reporter gene expression. The hKvβ1 full length and hKv1.1 (S4–S5) interaction was then evaluated for its ability to drive expression of a counter-selection reporter gene, as described above. Briefly, functional interaction of the expressed hKv1.1 and hKvβ1 domains was designed to reconstitute the function of the yeast Gal4 protein, driving expression of a downstream CYH2 (cyclohexamide sensitivity) reporter gene and conferring sensitivity to cycloheximide, thereby attenuating yeast cell growth on selective media. Disruption or inhibition of the protein-protein interaction between the expressed hKv1.1 and hKvβ1 domains prevented the functional reconstitution of the yeast Gal4 protein, allowing the yeast cells to grow (i.e., they are "rescued") on cyclohexamide-containing media (FIG. 5).

The human Kv1.1 potassium channel yeast strain (YKY4c/Kv1.1; $1\times10^5$ cells/ml) was embedded in selective media [SC-ura-leu-trp] containing 11 μg/ml cycloheximide. The negative control strain (CY856) was plated identically but at $2\times10^4$ cells/ml. Candidate compounds were applied (18 μg in 100% DMSO) to the agar surface using six 96-well microplate arrays per assay plate for a total of 576 compounds per assay plate. (Walsh, J., Proceeding: *Intl. Symp. Lab. Auto. Robotics*, Oct. 19–22, 1997, Boston, Mass.). Assay plates were incubated at 30° C. for 48 hours. Evidence of yeast growth at the point of compound application was scored visually and 'positive' compounds were retested in two additional assays to confirm activity (FIG. 5). All compounds were also tested against a negative control strain expressing an unrelated but interacting protein pair, plated under identical conditions (FIG. 6). Compounds that were selective for the Kv1.1/Kvβ1 strain were scored as active and analyzed in electrophysiological assays, as described below.

Compounds active in the yeast assay were examined for their ability to disrupt N-type Kv channel inactivation in CHO cells transfected with hKv1.1 alone, hKv1.1 plus hKvβ1, or hKv1.4, and in *Xenopus* oocytes injected with the corresponding mRNA's. As shown in FIG. 7, several of these compounds eliminated the rapid (N-type), Kvβ1-induced inactivation of Kv1.1. This "disinactivating" effect was potent and dose dependent, with an IC50 ranging from 0.3 μM to >100 μM in CHO cells and a 3–5 fold higher IC50 of 0.9 μM in oocytes. These compounds also eliminated N-type inactivation of hKv1.4 channels with a similar potency (IC50=2.5–18 μM). The compounds, however, had no effect on the inactivation kinetics of rKv4.2 channels (which inactivate by a combined N- and C-terminal mechanism), indicating that they selectively block N-type inactivation (FIG. 7). In addition to the disinactivating effect of these compounds, a parallel dose-dependent increase in peak current occurred simultaneously with the loss of inactivation. This increase in peak current is probably at least partially due to the removal of inactivation, which uncovers the "true" peak current of the channels in the cell, although other mechanisms such as a stabilization of the open state of the channel may also be occurring. At concentrations that eliminated N-type inactivation (up to 30 μM in CHO and 100 μM in oocytes) these compounds exhibited no effect on hKv1.1 channels expressed in the absence of hKvβ1 (FIG. 7). At 100 μM, however, Compound "A" blocked approximately 37% of the hKv1.1 current in CHO cells, thus high concentrations of some of these compounds are able to block Kv1.1 channels. Further analysis of Compound "A" using radioligand binding assays (NovaScreen, 7170 Standard Drive, Hanover, Md. 21076-1334) indicated that at concentrations up to 10 μM this compound had little or no affinity for neurotransmitter receptors, uptake sites, or other ion channels (including Na+ or Ca2+ channels).

The mechanism of action of these Kv channel modulators (referred to herein as "disinactivators") was further explored first by altering the voltage protocol so that single voltage steps to 50 mV were applied once every 20 sec (FIG. 8). This protocol significantly altered the IC50 for Compound "B" from 2.5 μM to 13.2 μM, thus indicating a use-dependence to the disinactivation. Second, it is known that N-terminal inactivating channel complexes are sensitive to the redox state of the intracellular medium. When glutathione was applied to maintain channels in their reduced (and inactivating) state, however, Compound "C" still disinactivated hKv1.4 in CHO cells (FIG. 8). Glutathione was able to block the disinactivation of the oxidizing agent $H_2O_2$, thus the "disinactivators" do not appear to disinactivate channels by oxidizing their N-terminals.

The activities of Kv channel modulators were examined in several in vitro and in vivo seizure models. Field potential recordings were performed in the CA1 region of rat hippocampal slices treated with 10 μM bicuculline to induce multiple population spikes (Albus, H. and R. Williamson, *Epilepsia* (1998) 39(2):124–139). Bath application of Compound "A" hippocampal slices dramatically reduced bicuculline-induced hyperexcitability (FIG. 9). These effects were similar to, though somewhat more rapid in onset and more potent than, the known anticonvulsant phenytoin, and suggested that the disinactivators were likely to have anticonvulsant activity in vivo. To test this hypothesis directly, the disinactivators were examined for their ability to protect mice from pentylenetetrazol-induced seizures. Mice were pretreated with Compound "D" or Compound "E" (30–300 mg/kg i.p.), valproic acid (156 mg/kg i.p.) or saline. Thirty minutes later, pentylenetetrazol (PTZ; 85 mg/kg, s.c.) was administered and the mice were monitored for development of spontaneous, recurrent seizures (a seizure was defined as loss of righting reflex; see Frey, H.-H. and I. Bartels, *Epilepsy Res.* (1997) 27:151–164). As shown in FIG. 10, Compound "D" and Compound "E" protected mice against PTZ-induced seizures, with estimated ED50s of 84 and 36 mg/kg I.P., respectively (ED50 for valproic acid=141 mg/kg I.P.). These compounds were also examined for their ability to block shock-induced seizures using the maximal electroshock paradigm. Interestingly, none of the disinactivators described above were active in this model, indicating that their efficacy against PTZ-induced seizures was not due to global suppression of neuronal excitability and that the disinactivators likely exert their effects on specific CNS pathways. The hippocampal slice and PTZ data demonstrate that inhibitors of N-type Kv channel inactivation ("disinactivators") inhibit seizure activity in vitro and in vivo.

As is evident from these examples, a functional interaction between the N-terminus of hKvβ1 and the cytoplasmic S4–S5 linker can be reconstituted in the yeast two-hybrid system, and small molecule inhibitors of this interaction ("disinactivators") eliminate N-type inactivation in cells coexpressing hKv1.1 and hKvβ1 or the related channel hKv1.4. Moreover, these disinactivators have potent activity in predictive preclinical anticonvulsant models, suggesting that they may have therapeutic utility in treating specific types of human epilepsy. These disinactivators represent an entirely new pharmacological class of ion channel modulators that can be used to probe the role of N-type channel inactivation in native cells and tissues and may lead to improved mechanism-based therapeutics for neurodegenerative diseases and epilepsy.

Example 4

Signal Transduction Pathway Screen

This example demonstrates the non-transcription (or transcription independent) based two-hybrid system for identifying modulators of N-type ion channel inactivation using a signal transduction pathway screen. In this non-transcription based system, the modified host cell contains a first hybrid protein comprising an intracellular receptor region of an α-subunit of a voltage-gated ion channel in polypeptide linkage to a first peptide of a peptide binding pair, and a second hybrid protein comprising an amino-terminal inactivation region of an ion channel protein in polypeptide linkage to a second peptide of the peptide binding pair, wherein binding interaction between the two peptides causes activation of a signal transduction pathway in the modified host cell. Activation of the signal transduction pathway does not occur in the presence of a molecule which inhibits binding of the intracellular receptor region and the amino-terminal inactivation region of an ion channel protein.

A. Kv1.1/β1 Yeast Two-Hybrid Screen:

The standard methods used to generate recombinant reagents are as described in Example 1 above.

Kv1.1 alpha S4–5 loop: The cDNA encoding the intracellular loop between S4 and S5 transmembrane domains of the Kv1.1 potassium channel alpha subunit are generated as oligonucleotides. A 59 base sense oligonucleotide is generated with a 5' precut EcoRI site, a stop codon and a 3' precut XhoI site which has the following sequence:

[SEQ. ID NO:20]
5'-AA TTC CTC TTC ATC GGG GTC ATC CTG TTT TCT AGT
    GCA GTG TAC TTT GCC GAG TAA GCC-3' and a 59 base reverse compliment oligonucleotide containing a 5' precut XhoI site, a stop codon, and a 3' precut EcoRI site which has the following sequence:

[SEQ. ID NO:21]
5'-T CGA GGC TTA CTC GGC AAA GTA CAC TGC ACT AGA
    AAA CAG GAT GAC CCC GAT GAA GAG G-3'

The oligonucleotides are phosphorylated and annealed by standard techniques and cloned into the EcoRI-XhoI site of pMyr vector (Strategene, La Jolla, Calif. 92037) to generate S45-pMyr.

In a similar manner, complimentary oligonucleotides are generated encoding precut BamHI, S4–S5 loop, stop codon and precut Sal I sites for cloning into the BamHI-SalI sites of pSOS vector (Stratagene, La Jolla, Calif. 92037).

Kvb1 full length: The cDNA encoding the full length β1 cytoplasmic protein is generated by PCR using a 39 base sense oligonucleotide containing a 5' BamHI site with the following sequence:

[SEQ. ID NO:22]
5'-AGT AGG ATC CCC ATG CCA GTC TCC ATA GCC TGC ACA
    GAG-3' and a 39 base antisense oligonucleotide containing a stop codon and a Sal I site having the following sequence:

[SEQ. ID NO:23]
5'-GGG ACG TCG ACG CCA TTA TGA TCT ATA GTC CTT CTT
    GCT-3' and Kvβ1 as template (Genbank Accession No. U33428). The 1205 basepair product encodes bp 28–1233 of human Kvβ1. The cDNA is cloned into the BamHI-Sal I site of pSOS vector (Strategene, La Jolla, Calif.) as a 3' fusion to hSOS and generated recombinant plasmid Kvβ1-pSOS.

In a similar manner, an sense oligonucleotide is generated containing a EcoRI site and an antisense oligonucleotide containing a Sal I site are used to generate a Kvβ1 PCR product which is directionally cloned into the EcoRI-Sal I site of pMyr to generated Kvβ1-pMyr.

B. Bioassay Conditions:

The plasmids generated for the non-transcription based two-hybrid system are used to generate appropriate experimental and control yeast strains. All strains are generated by transforming the above described expression plasmids into yeast strain cdc25H (Strategene, La Jolla, Calif.) using a lithium chloride method and grown on synthetic drop-out media to maintain plasmids, as described in Example 2 above. Interaction is tested by plating yeast strains harboring plasmid combinations on selective media (SD glucose vs SD galactose) and assayed for growth at 25° C. and 37° C., as described in Cytotrap Vector Kit, Strategene catalog no. 217438; Karin et al., U.S. Pat. No. 5,776,689; and Aronheim et al., *Mol. Cell. Biol.* (1997) 17:3094–3102. Strains that contain a functional interaction fusion protein pair demon strate growth at 25° C. on both glucose and galactose containing media, and at 37° C. on galactose containing media. Yeast strains containing only one fusion protein or a non-interacting peptide pair demonstrate growth on glucose or galactose containing plates at 25° C., but fail to grow on either media at 37° C.

| Strains: | |
|---|---|
| S45-pMyr and β1-pSOS | (strain YKY/1NtKv1.1) |
| S45-pMyr and pSOS | (strain YKY/2NtKv1.1) |
| pMyr and β1 pSOS | (strain YKY/3NtKv1.1) |
| β1-pMyr and S45-pSOS | (strain YKY/4NtKv1.1) |
| β1-pMyr and pSOS | (strain YKY/5NtKv1.1) |
| pMyr and S45-pSOS | (strain YKY/6NtKv1.1) |

The above-described system is also useful for identifying compounds capable of disruption of the S4–S5 loop and β1 protein (i.e., "disinactivators"), wherein disruption of interaction is identified by lack of cell growth at 37° C., or by growth using a pathway responsive inverse selection reporter.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A non-naturally occurring polynucleotide encoding a fusion protein which comprises:
    an S4–S5 cytoplasmic loop of an ion channel; and
    a DNA-binding or transcription activation domain of a transcriptional activator,
    wherein said S4–S5 cytoplasmic loop comprises SEQ ID NO:1 and is an S4–S5 cytoplasmic loop of an α-subunit of a potassium channel, and wherein said potassium channel is selected from the group consisting of Kv1.1, Kv1.2, Kv1.3, Kv1.4, Kv1.5, Kv1.6, and Kv3.4.

2. A non-naturally occurring polynucleotide encoding a fusion protein which comprises:
    an S4–S5 cytoplasmic loop of an ion channel; and
    a DNA-binding or transcription activation domain of a transcriptional activator,
    wherein said S4–S5 cytoplasmic loop comprises SEQ ID NO:2 and is an S4–S5 cytoplasmic loop of an α-subunit of a potassium channel, and wherein said potassium channel is selected from the group consisting of Kv1.1, Kv1.2, Kv1.3, Kv1.4, Kv1.5, Kv1.6, and Kv3.4.

3. A non-naturally occurring polynucleotide encoding a fusion protein which comprises:
    an amino-terminal inactivation region of an ion channel; and
    a DNA-binding or transcription activation domain of a transcriptional activator,
    wherein said amino-terminal inactivation region comprises SEQ ID NO:5 and is an amino-terminal inactivation region of a potassium channel α- or β-subunit, and wherein said potassium channel α- or β-subunit is selected from the group consisting of Kvβ1, Kvβ1.2, Kvβ1.3, Kvβ3, Kv3.4, and Kv1.4.

4. A non-naturally occurring polynucleotide encoding a fusion protein which comprises:
    an amino-terminal inactivation region of an ion channel; and
    a DNA-binding or transcription activation domain of a transcriptional activator,
    wherein said amino-terminal inactivation region comprises SEQ ID NO:6 and is an amino-terminal inactivation region of a potassium channel α- or β-subunit, and wherein said potassium channel α- or β-subunit is selected from the group consisting of Kvβ1, Kvβ1.2, Kvβ1.3, Kvβ3, Kv3.4, and Kv1.4.

* * * * *

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 16 amino acids
      (B) TYPE: amino acid
      (C) STRANDEDNESS: not relevant
      (D) TOPOLOGY: not relevant (ii) MOLECULE TYPE: peptide (vi) ORIGINAL SOURCE:
      (A) ORGANISM: Homo sapiens (xi) SEQUENCE DESCRIPTION: SEQ ID NO: 1:

Gln Ile Leu Gly Gln Thr Leu Lys Ala Ser Met Arg Glu Leu Gly Le
1           5                10              15

(2) INFORMATION FOR SEQ ID NO: 2:

(i) SEQUENCE CHARACTERISTICS:
      (A) LENGTH: 16 amino acids
      (B) TYPE: amino acid
      (C) STRANDEDNESS: not relevant
      (D) TOPOLOGY: not relevant (ii) MOLECULE TYPE: peptide (vi) ORIGINAL SOURCE:
      (A) ORGANISM: Homo sapiens (xi) SEQUENCE DESCRIPTION: SEQ ID NO: 2:

Gln Ile Leu Gly His Thr Leu Arg Ala Ser Met Arg Glu Leu Gly Le
1           5                10              15

(2) INFORMATION FOR SEQ ID NO: 3:

(i) SEQUENCE CHARACTERISTICS:
      (A) LENGTH: 48 base pairs
      (B) TYPE: nucleic acid
      (C) STRANDEDNESS: single
      (D) TOPOLOGY: linear -continued (ii) MOLECULE TYPE: DNA (genomic)

(xi) SEQUENCE DESCRIPTION: SEQ ID NO: 3:

GATCCTGGGC CAGACCCTCA AAGCTAGTAT GAGAGAGCTA GGGCTGCT          48

(2) INFORMATION FOR SEQ ID NO: 4:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

GATCCTGGGC CACACCCTCA GAGCCAGCAT GCGGGAACTG GGCCTTCT          48

(2) INFORMATION FOR SEQ ID NO: 5:

(i) SEQUENCE CHARACTERISTICS:
        (A) LENGTH: 30 amino acids
        (B) TYPE: amino acid
        (C) STRANDEDNESS: not relevant
        (D) TOPOLOGY: not relevant (ii) MOLECULE TYPE: peptide (vi) ORIGINAL SOURCE:
        (A) ORGANISM: Homo sapiens (xi) SEQUENCE DESCRIPTION: SEQ ID NO: 5:

Met Gln Val Ser Ile Ala Cys Thr Glu His Asn Leu Lys Ser Arg As
1          5                  10               15

Gly Glu Asp Arg Leu Leu Ser Lys Gln Ser Ser Thr Ala Pro
        20                25              30

(2) INFORMATION FOR SEQ ID NO: 6:

(i) SEQUENCE CHARACTERISTICS:
        (A) LENGTH: 30 amino acids
        (B) TYPE: amino acid
        (C) STRANDEDNESS: not relevant
        (D) TOPOLOGY: not relevant (ii) MOLECULE TYPE: peptide (vi) ORIGINAL SOURCE:
        (A) ORGANISM: Homo sapiens (xi) SEQUENCE DESCRIPTION: SEQ ID NO: 6:

Met Glu Val Ala Met Val Ser Ala Glu Ser Ser Gly Cys Asn Ser Hi
1          5                  10               15

Met Pro Tyr Gly Tyr Ala Ala Gln Ala Arg Ala Arg Glu Arg
        20                25              30

(2) INFORMATION FOR SEQ ID NO: 7:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

ATGCAAGTCT CCATAGCCTG CACAGAGCAC AATTTGAAGA GTCGGAATGG TGAGGACCGA      60

CTTCTGAGCA AGCAGAGCTC CACCGCCCCC                                        90

(2) INFORMATION FOR SEQ ID NO: 8:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

ATGGAGGTTG CAATGGTGAG TGCGGAGAGC TCAGGGTGCA ACAGTCACAT GCCTTATGGT        60

TATGCTGCCC AGGCCCGGGC CCGGGAGCGG                                        90

(2) INFORMATION FOR SEQ ID NO: 9:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CATGGAGCTC TTCATCGGGG TCATCCTGTT TTCTAGTGCA GTGTACTTTG CCGAGTAAG        59

(2) INFORMATION FOR SEQ ID NO: 10:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

GATCCTTACT CGGCAAAGTA CACTGCACTA GAAAACAGGA TGACCCCGAT GAAGAGCTC        59

(2) INFORMATION FOR SEQ ID NO: 11:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

CCGAATTCGA CATATGAAAA TGCAAGTCTC CATAGCCTGC ACAGAGCACA ATTTG            55

(2) INFORMATION FOR SEQ ID NO: 12:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

ACGGATCCCC GAATTCCATT ATGATCTATA GTCCTTCTTG CT                           42

(2) INFORMATION FOR SEQ ID NO: 13:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

ACGGATCCCC GAATTCCATT AATCTGAAAT TGACCTCCA AATGT             45

(2) INFORMATION FOR SEQ ID NO: 14:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

CATGGAGCAG ATCCTGGGCC ACACCCTGAG AGCCAGCATG CGGGAACTGG GCCTTTAAG     59

(2) INFORMATION FOR SEQ ID NO: 15:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

GATCCTTAAA GGCCCAGTTC CGGCATGCTG GCTCTGAGGG TGTGGCCCAG GATCTGCTC     59

(2) INFORMATION FOR SEQ ID NO: 16:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

CGAATTCATA TGCGGATCCG TAGAATGGAG GTTGCAATGG TGAGTGCGGA GAGCTCAGGG     60

(2) INFORMATION FOR SEQ ID NO: 17:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GGTCGACGAA TTCGTTACCT TGCAGGATCG GAGCTCTCGT G               41

(2) INFORMATION FOR SEQ ID NO: 18:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

CATGGAGCAG ATCCTGGGCC ACACCCTCAG AGCCAGCATG CGGCAACTGG GCCTTTAAG          59

(2) INFORMATION FOR SEQ ID NO: 19:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

GATCCTTAAA GGCCCAGTTG CCGCATGCTG GCTCTGAGGG TGTGGCCCAG GATCTGCTC          59

(2) INFORMATION FOR SEQ ID NO: 20:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

AATTCCTCTT CATCGGGGTC ATCCTGTTTT CTAGTGCAGT GTACTTTGCC GAGTAAGCC          59

(2) INFORMATION FOR SEQ ID NO: 21:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

TCGAGGCTTA CTCGGCAAAG TACACTGCAC TAGAAAACAG GATGACCCCG ATGAAGAGG          59

(2) INFORMATION FOR SEQ ID NO: 22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

AGTAGGATCC CCATGCCAGT CTCCATAGCC TGCACAGAG          39

(2) INFORMATION FOR SEQ ID NO: 23:

(i) SEQUENCE CHARACTERISTICS:
        (A) LENGTH: 39 base pairs
        (B) TYPE: nucleic acid
        (C) STRANDEDNESS: single

```
            (D) TOPOLOGY: linear (ii) MOLECULE TYPE: DNA (genomic)

(xi) SEQUENCE DESCRIPTION: SEQ ID NO: 23:

GGGACGTCGA CGCCATTATG ATCTATAGTC CTTCTTGCT                                          39
```